(12) United States Patent
Grubsky et al.

(10) Patent No.: US 9,250,200 B1
(45) Date of Patent: Feb. 2, 2016

(54) COMPTON TOMOGRAPHY SYSTEM

(75) Inventors: Victor Grubsky, Porter Ranch, CA (US); Volodymyr Romanoov, Torrance, CA (US); Keith Shoemaker, Harbor City, CA (US); Edward Matthew Patton, Torrance, CA (US); Tomasz Jannson, Torrance, CA (US)

(73) Assignee: Physical Optics Corporation, Torrance, CA (US)

( * ) Notice: Subject to any disclaimer, the term of this patent is extended or adjusted under 35 U.S.C. 154(b) by 427 days.

(21) Appl. No.: 13/586,682

(22) Filed: Aug. 15, 2012

Related U.S. Application Data

(60) Provisional application No. 61/523,792, filed on Aug. 15, 2011.

(51) Int. Cl.
*G01N 23/04* (2006.01)
*G21K 1/02* (2006.01)

(52) U.S. Cl.
CPC ............... *G01N 23/046* (2013.01); *G21K 1/02* (2013.01)

(58) Field of Classification Search
CPC ............... G01V 5/0025; G01N 23/10; G01N 2223/615; A61B 6/5282
USPC ............... 378/57, 86, 87, 88, 89, 90
See application file for complete search history.

(56) References Cited

U.S. PATENT DOCUMENTS

| | | | |
|---|---|---|---|
| 5,696,806 A | 12/1997 | Grodzins et al. | |
| 5,930,325 A | 7/1999 | Momose | |
| 5,930,326 A | 7/1999 | Rothschild et al. | |
| 5,930,327 A | 7/1999 | Lin | |
| 5,930,328 A | 7/1999 | Nakamura et al. | |
| 2010/0027749 A1* | 2/2010 | Ledoux et al. | 378/88 |
| 2012/0224669 A1* | 9/2012 | Ledoux et al. | 378/41 |

OTHER PUBLICATIONS

R. Accorsi, Design of Near-Field Coded Aperture Cameras for High-resolution Medical and Industrial Gamma-ray Imaging, Massachusetts Institute of Technology, Department of Nuclear Engineering, 2001, Ph.D. Thesis.

* cited by examiner

*Primary Examiner* — Hoon Song
(74) *Attorney, Agent, or Firm* — Sheppard Mullin Richter & Hampton LLP

(57) ABSTRACT

A Compton tomography system comprises an x-ray source configured to produce a planar x-ray beam. The beam irradiates a slice of an object to be imaged, producing Compton-scattered x-rays. The Compton-scattered x-rays are imaged by an x-ray camera. Translation of the object with respect to the source and camera or vice versa allows three-dimensional object imaging.

36 Claims, 17 Drawing Sheets

Cylindrical CA, Object at Infinity

Apodized CA, Object at Infinity

Cylindrical CA, Object at 400 mm to CA

Apodized CA, Object at 400 mm to CA

Cylindrical CA, Object at 200 mm to CA

Apodized CA, Object at 200 mm to CA

COMPTON TOMOGRAPHY SYSTEM

CROSS-REFERENCE TO RELATED APPLICATIONS

This application claims the benefit of U.S. Provisional Application No. 61/523,792, filed Aug. 15, 2011, which is hereby incorporated herein by reference in its entirety.

STATEMENT OF RIGHTS TO INVENTIONS MADE UNDER FEDERALLY SPONSORED RESEARCH

Aspects of the invention(s) disclosed herein were made with Government support under: Contract No. W31P4Q-09-C-0091 awarded by the Army; Grant No. DE-SC0003345 awarded by the Department of Energy; Contract No. FA8501-10-C-0034 awarded by the Air Force; and Contract No. NNX12CF40P. The Government has certain rights in the invention(s).

TECHNICAL FIELD

The present invention relates generally to non-destructive three-dimensional (3D) object structure acquisition, and more particularly, some embodiments relate to tomography.

DESCRIPTION OF THE RELATED ART

Conventional x-ray computed tomography (CT) systems perform 3D object structure acquisition by measuring the object's transmission of x-ray in multiple (180-360) directions (angles) and applying a Radon transform to the data. To scan the object with x-rays at multiple directions, either the object or the source/camera assembly are rotated, which requires a large gantry for accommodating large objects. Such a complicated setup also makes it nearly impossible to scan large or stationary objects. Additionally, conventional CT systems require large-area detectors because a diverging x-ray beam is typically used. Finally, the conventional CT approach does not produce high-contrast images in low-Z (for example, organic) materials, which have relatively small x-ray absorption.

Another x-ray tomography approach is based on the detection of x-ray photons Compton-scattered by the object. This approach takes advantage of the fact that, given a uniform x-ray beam, the intensity of the Compton scattering is proportional to the local electron density of the material, which is closely related to the material's physical density. Therefore, by mapping the distribution of Compton scattering intensity within the object, one can reconstruct the density distribution. In such systems, the object is scanned with a thin and collimated beam ("pencil beam") of x-rays and a line sensor in combination with a collimator is used to measure the Compton scattering intensity distribution along the irradiated line. Although such a Compton tomography technique allows one-sided inspection of large objects, it has a slow acquisition process (due to point-by-point scanning) and the need for a two-dimensional (2D) beam or object displacement to complete a full scan.

BRIEF SUMMARY OF EMBODIMENTS OF THE INVENTION

Some aspects of the disclosure present methods and apparatuses for quick and efficient 3D object structure acquisition based on Compton x-ray tomography, which would be amenable to one-sided scanning (i.e., without requiring two-sided access required in for conventional CT) of large objects and at the same time require only relatively compact hardware.

Other features and aspects of the invention will become apparent from the following detailed description, taken in conjunction with the accompanying drawings, which illustrate, by way of example, the features in accordance with embodiments of the invention. The summary is not intended to limit the scope of the invention, which is defined solely by the claims attached hereto.

BRIEF DESCRIPTION OF THE DRAWINGS

The present invention, in accordance with one or more various embodiments, is described in detail with reference to the following figures. The drawings are provided for purposes of illustration only and merely depict typical or example embodiments of the invention. These drawings are provided to facilitate the reader's understanding of the invention and shall not be considered limiting of the breadth, scope, or applicability of the invention. It should be noted that for clarity and ease of illustration these drawings are not necessarily made to scale.

Some of the figures included herein illustrate various embodiments of the invention from different viewing angles. Although the accompanying descriptive text may refer to such views as "top," "bottom" or "side" views, such references are merely descriptive and do not imply or require that the invention be implemented or used in a particular spatial orientation unless explicitly stated otherwise.

Figure 1:
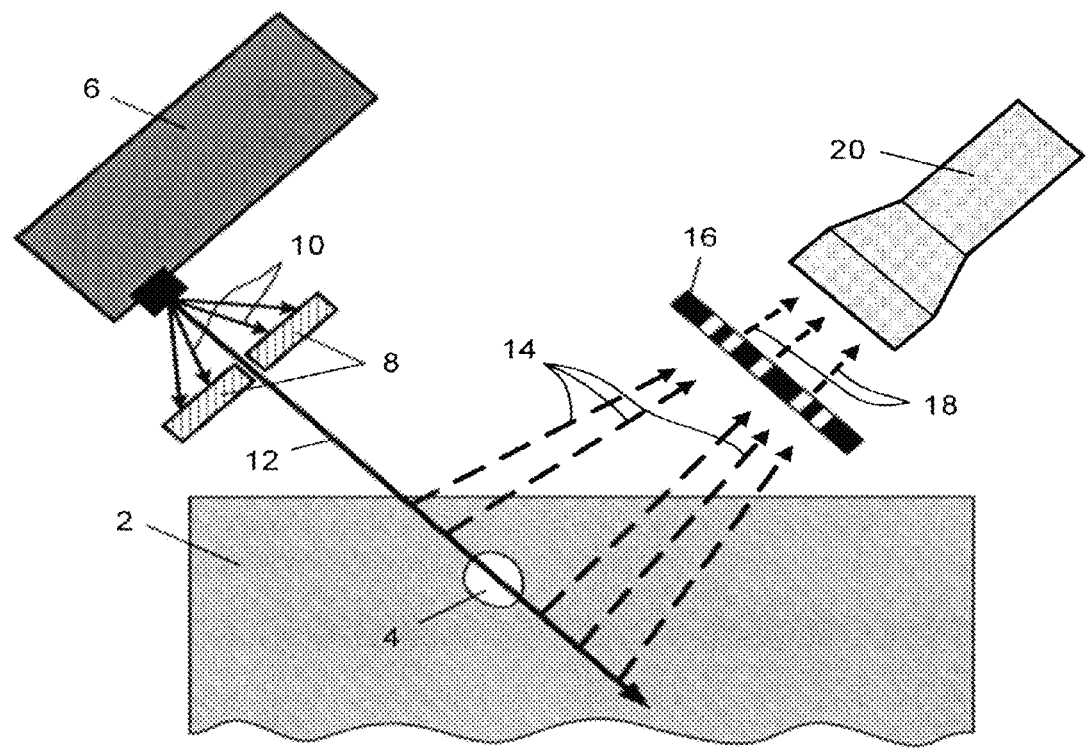
FIG. 1 is a side view of a Compton tomography system according to the present invention.

The figures are not intended to be exhaustive or to limit the invention to the precise form disclosed. It should be understood that the invention can be practiced with modification and alteration, and that the invention be limited only by the claims and the equivalents thereof.

DETAILED DESCRIPTION OF THE EMBODIMENTS OF THE INVENTION

Some embodiments of the invention provide a method and apparatus for quick and efficient 3D object structure acquisition based on Compton x-ray tomography, which would be amenable to one-sided scanning (i.e., without requiring two-sided access required in for conventional CT) of large objects and at the same time require only relatively compact hardware.

Embodiments further provide a device for efficient collection and imaging of Compton-scattered x-rays, produced by irradiated consecutive 2D planar cross sections of the object, onto an x-ray camera.

Additionally, embodiments provide a technique for true determination of 3D internal structure of an object based on the raw data acquired by Compton tomography technique of this invention.

In these embodiment, Compton tomographic 3D data acquisition is accomplished by irradiating the object with a sheet-liked x-ray beam (such as a planar x-ray beam), and recording the resulting 2D Compton-scattered images of consecutively irradiated cross sections (or two-dimensional subsets, when a non-planar sheet-like beam is used) of the object with an x-ray camera, for multiple sequential beam or object positions. The sheet-like x-ray beam is generated by passing a divergent conical beam, generated with an x-ray source, through a slit collimator fabricated of a material with high x-ray absorption. In some cases, the slit collimator is a straight slit producing a planar x-ray beam. The irradiated cross section (slice) of the object emits Compton-scattered x-ray photons, with intensity distribution proportional to the local electron density of the object cross section. The Compton scattering distribution is imaged onto an x-ray camera using special apodized aperture x-ray optics, having one or multiple apertures with depth-dependent profile (apodization). The 3D structure information is acquired by translating the object in one direction with respect to the source/camera assembly, or vice versa. The system is well suited for one-sided data acquisition because the x-ray source, x-ray optics, and camera can all be disposed on the same side of the object.

X-rays, as the term is used herein, are photons with energies in excess of 1 keV, regardless of the nature of their generation. In this disclosure, an x-ray source is any device capable of generating x-ray photons, according to the above definition. For photons with energies 1-500 keV, the typical source would be a conventional x-ray tube with appropriate accelerating voltage (up to 500 kV). Higher energy photons (500 keV-20 MeV), capable of deeper penetration into sample material, can be produced with a linear accelerator. Alternatively, a radioisotope source, such as a Co-60 gun, can be employed for x-ray (gamma-ray) photon generation.

Figure 2A:
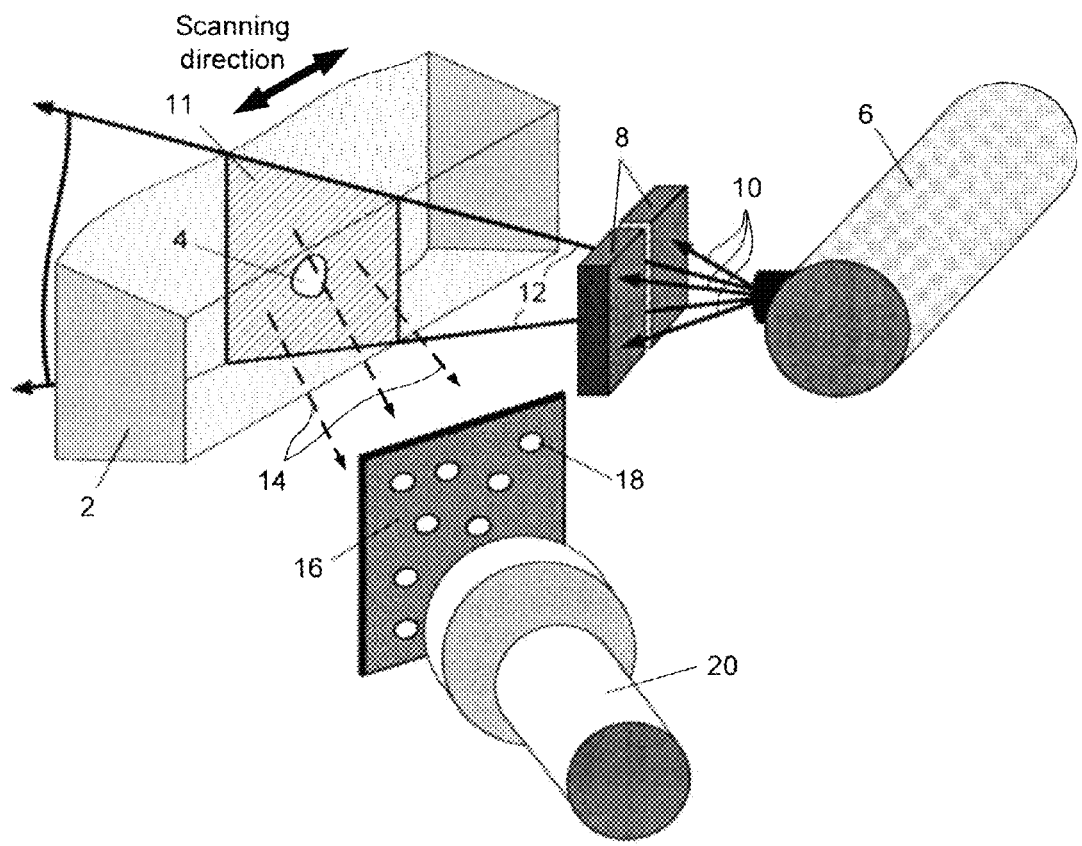
FIG. 2A is a perspective view of a Compton tomography system of FIG. 1.

FIG. 1 illustrates a side view of an example Compton tomography system. FIG. 2A illustrates a perspective view of the example Compton tomography system. The system includes an x-ray source 6 and an x-ray camera 20. The illustrated system is used to image an object, such as sample 2, with internal electron density differences (for example, because of defect 4). The x-ray source 6 may comprise any system capable of generating x-ray photons. For photons with energies 1-500 keV, the typical source would be a conventional x-ray tube with appropriate accelerating voltage (up to 500 kV). Higher energy photons (500 keV-20 MeV), capable of deeper penetration into sample material, can be produced with a linear accelerator. Alternatively, a radioisotope source, such as a Co-60 gun, can be employed for x-ray (gamma-ray) photon generation.

The x-ray source 6 may operate at an appropriate x-ray photon energy. The appropriate x-ray photon energy may be determined based on the properties and dimension of the tested sample 2. Because the attenuation of x-rays in materials generally decreases with photon energy, it is advantageous to use high-energy photons to achieve high penetration capability, especially when working with thick samples. Based on experimental results, the typical penetration depth $L_p$ of this Compton tomography technique is approximately given by:

$$L_p \approx 3 L_{att}, \quad (1)$$

where $L_{att}$ is the photon-energy-dependent x-ray attenuation length in the material:

$$L_{att} = \frac{1}{\rho(\sigma_{abs} + \sigma_{sc} + \sigma_{pp})}. \quad (2)$$

Figure 3:
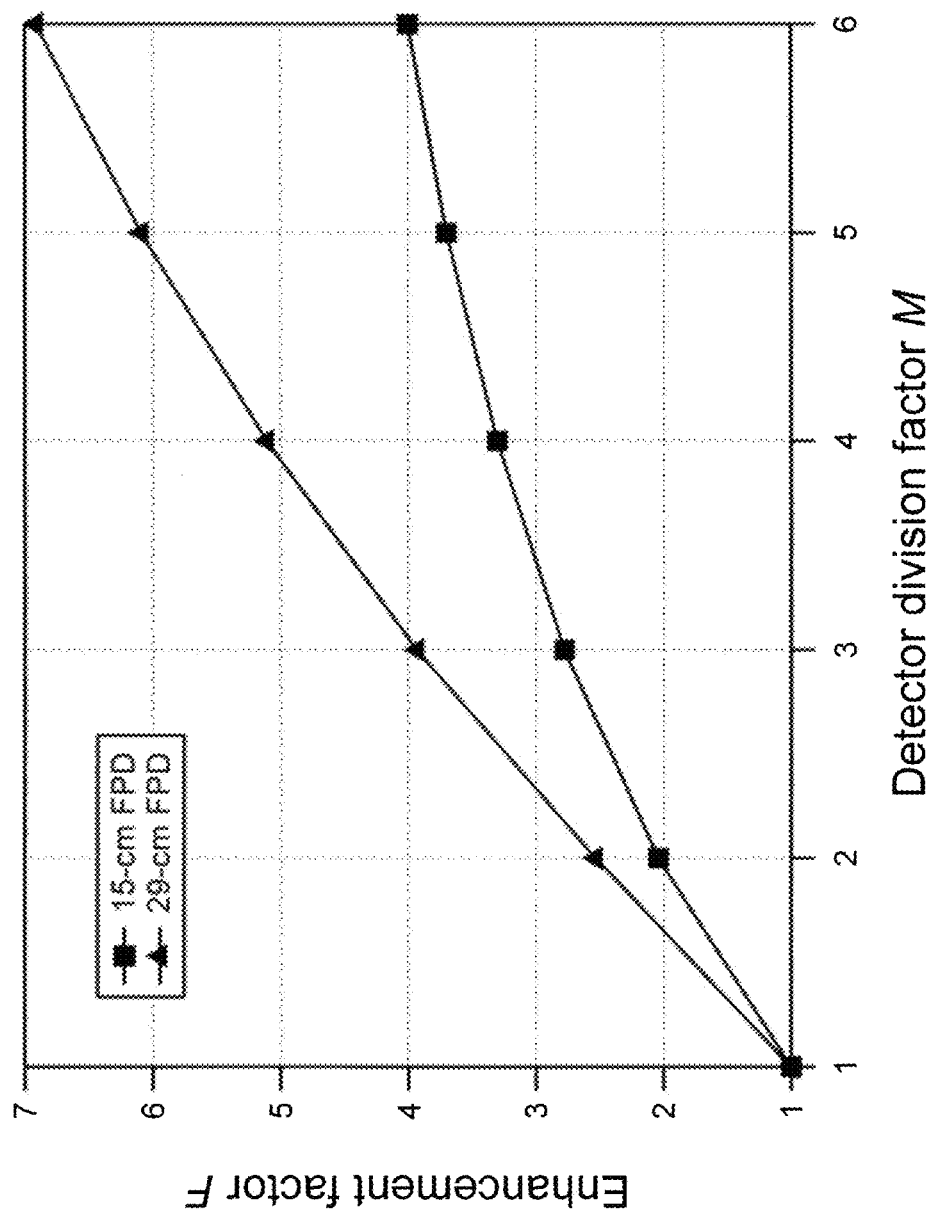
FIG. 3 illustrates the image figure-of-merit enhancement factor for large x-ray detectors in the multiple-imaging configuration, compared to using the same detectors in a single-imaging configuration, as a function of the detector division factor.
Figure 4:
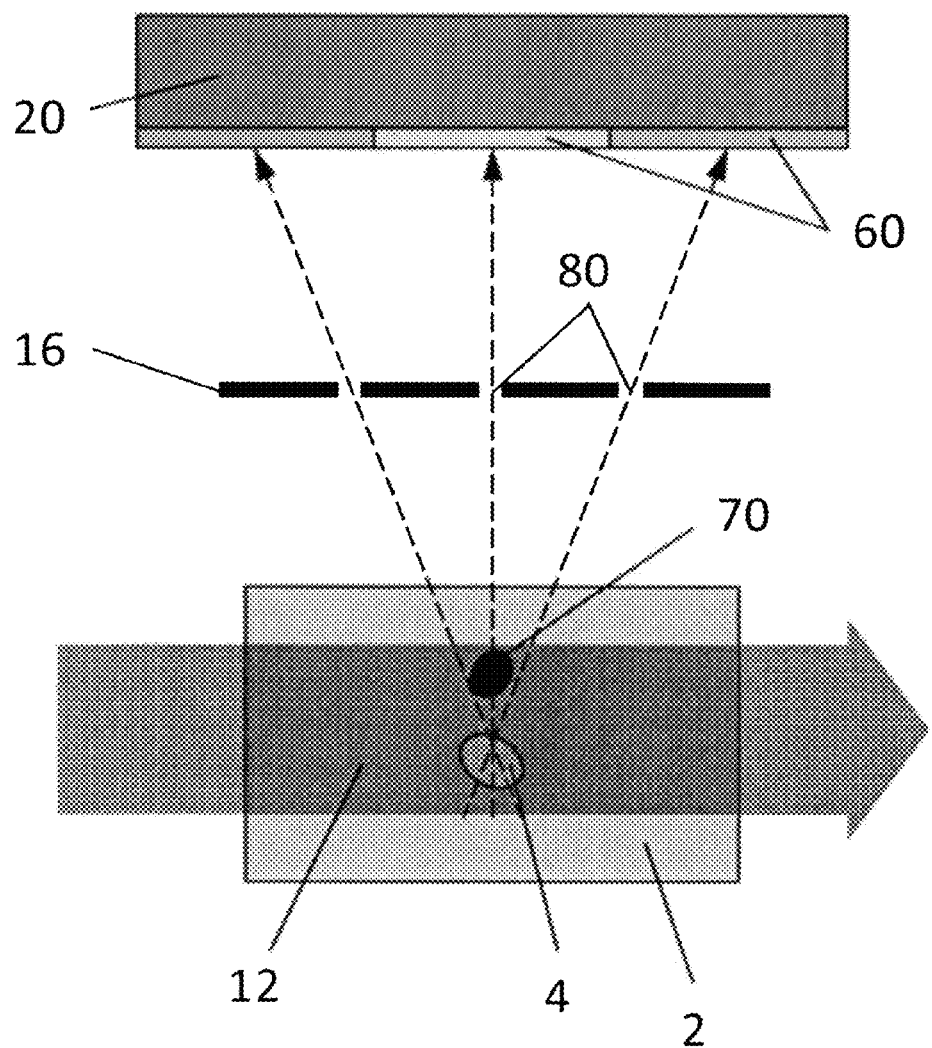
FIG. 4 illustrates the effect of the stereoscopic image recording by a large x-ray detector in the multiple-imaging configuration.
Figure 5:
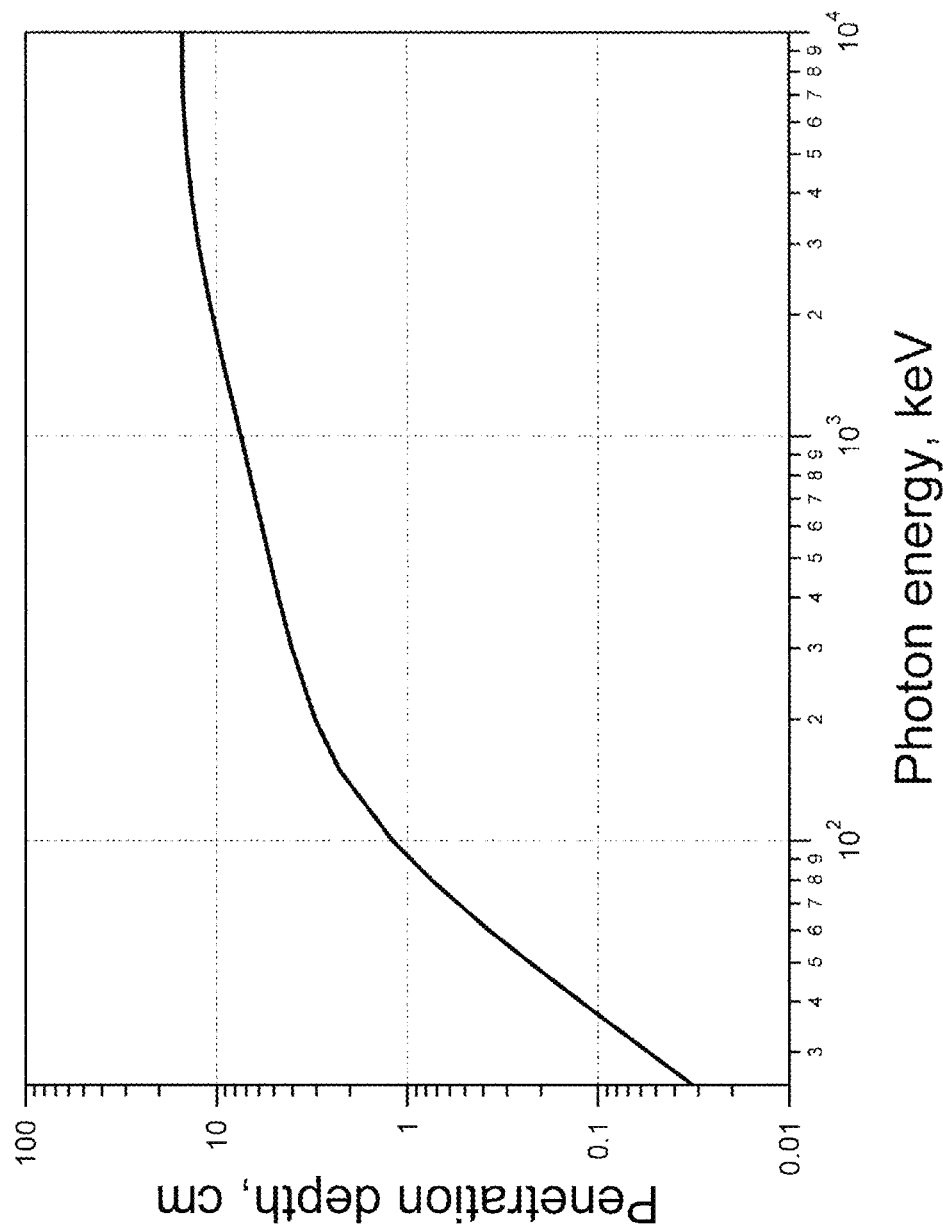
FIG. 5 is the graph of the penetration depth in steel, vs. x-ray photon energy, for the Compton tomography system of FIG. 1.

Here, $\rho$ is the sample average density, $\sigma_{abs}$ is the x-ray photoelectric absorption cross section, $\sigma_{sc}$ is the combined scattering cross section (which includes both Compton and elastic scattering), and $\sigma_{pp}$ is pair production cross section (significant only for photon energies in excess of 1 MeV). As an example, FIG. 5 illustrates the penetration depth in steel as a function of photon energy. The penetration depth in steel is just over 1 cm for 100-keV photons, and approximately 10 cm for 20-MeV photons (FIG. 3).

Figure 6:
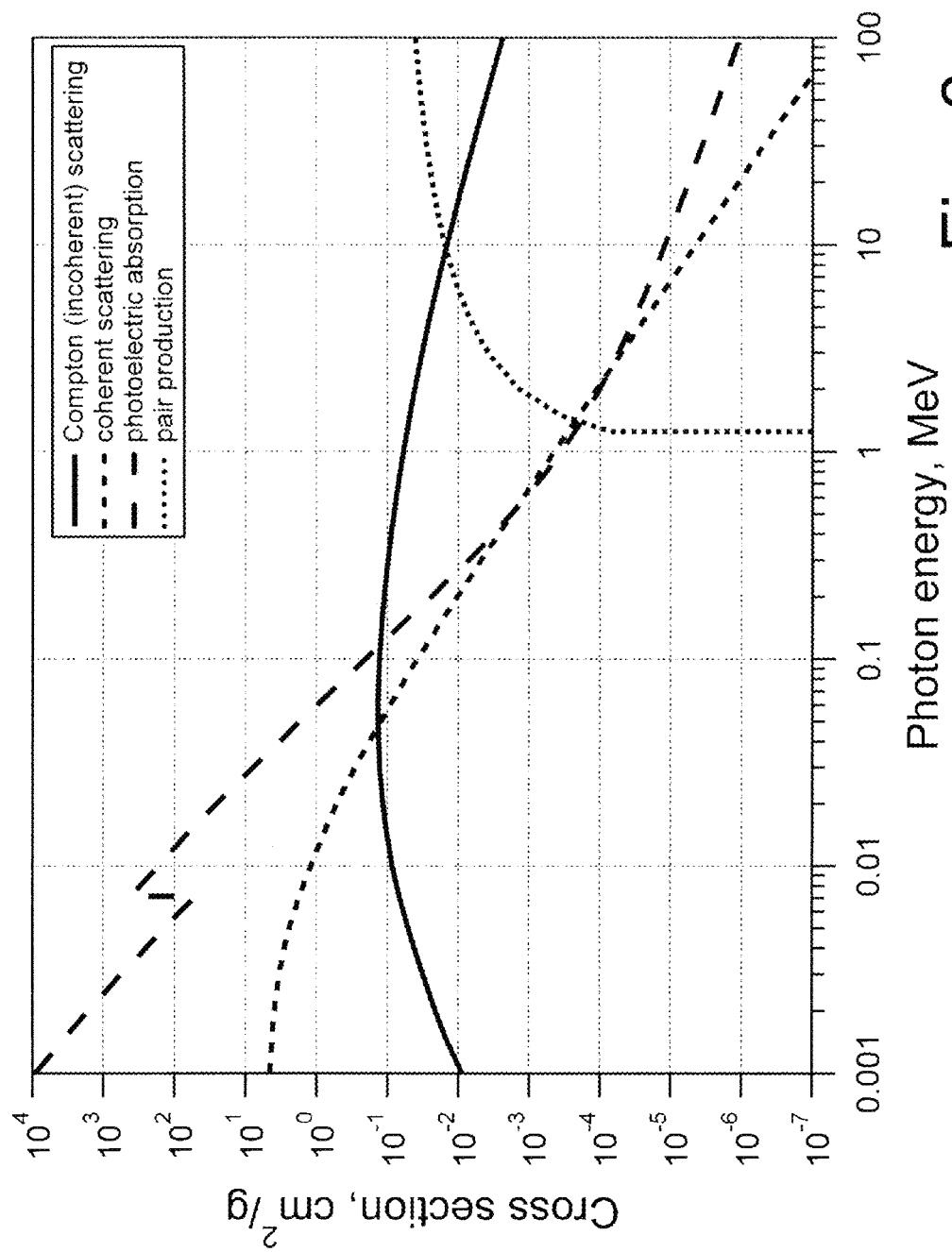
FIG. 6 is the graph of the cross sections for various types of x-ray interactions in steel, vs. x-ray photon energy.

Another important consideration in choosing the photon energy for Compton tomography is the minimization of the probability of various other x-ray interaction mechanisms, such as photoelectric absorption, elastic scattering, and pair production. As shown in FIG. 6, using steel as an example, Compton scattering remains the dominant mechanism of interaction for photon energies in the range of 100 keV-10 MeV, which is often referred to as "Compton window." Operation within this photon energy range is advantageous because it reduces wasteful x-ray beam attenuation and so improves the signal strength.

Figure 7:
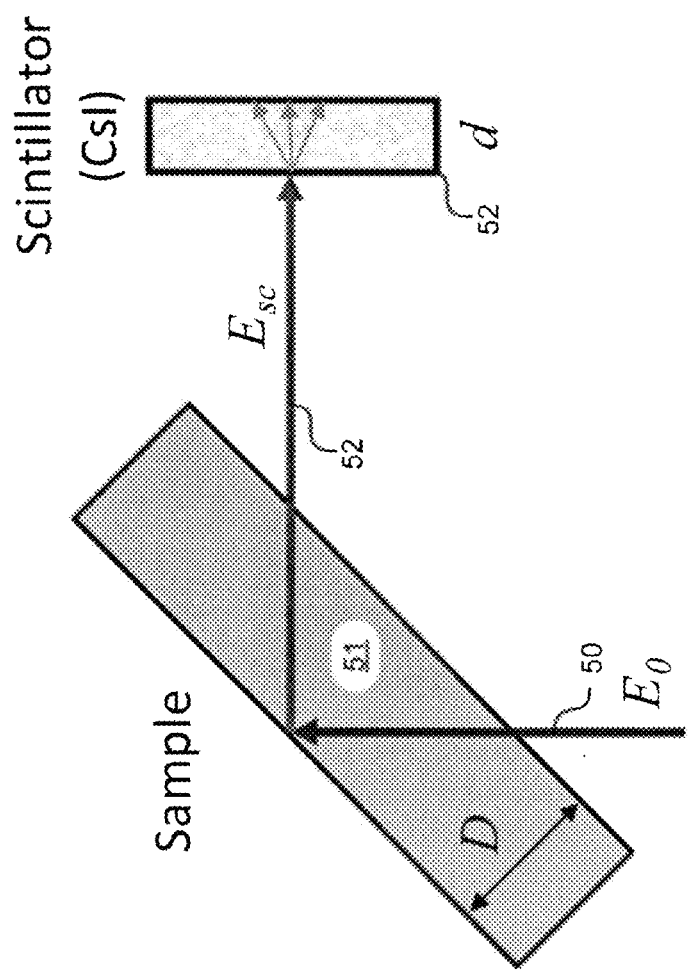
FIG. 7 is an illustration of source, sample, and scattering beam geometry.

Additionally, the x-ray source 6 may operate at an optimum photon energy, or at a predetermined range of energies encompassing the optimum photon energy. For a given object properties and detector configuration, there is an optimum photon energy that depends on the following factors. In the following example of optimizing the x-ray photon energy, we consider the geometry shown in FIG. 7. A photon 50 with energy $E_0$ is impinging on a layer of material 51 with depth D (1 in. of Al in this example) at 45° to the surface. The energy of the scattered photon 52 is:

$$E_{sc} = E_0 P(E_0), \text{ where } P(E_0) = \frac{1}{1 + \frac{E_0}{m_e c^2}}. \quad (3)$$

The Compton cross section for side scattering at 90° is:

$$\frac{d\sigma_{sc}}{d\Omega} = \frac{r_e^2}{2} P^2(E_0) \left[ P(E_0) + \frac{1}{P(E_0)} - 1 \right]. \quad (4)$$

The total photon attenuation upon entering and exiting from the material is:

$$\alpha = \exp\{-D\sqrt{2}[\mu(E_0) + \mu(E_{sc})]\}. \quad (5)$$

The scattered photon 52 then impinges a detector (here a scintillator 52 with thickness d). The fraction of energy absorbed in the scintillator (1-mm cesium iodide layer):

$$\epsilon = 1 - \exp[-\mu_{en}(E_{sc})d]. \quad (6)$$

Finally, the total photon efficiency is:

$$\eta \sim \alpha \epsilon \frac{d\sigma_{sc}}{d\Omega}. \quad (7)$$

Figure 8:
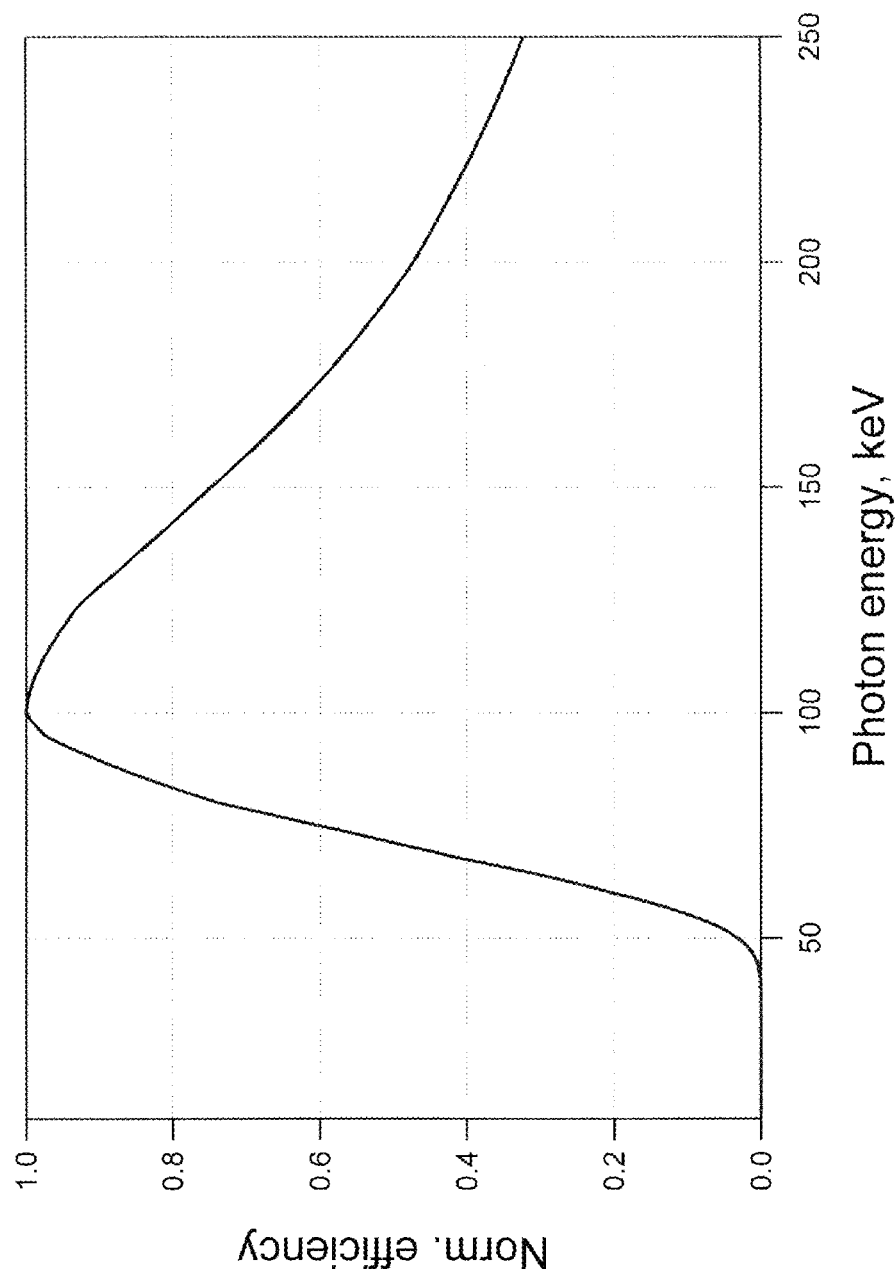
FIG. 8 is an illustration of normalized efficiencies vs. photon energy for example system parameters.

This quantity is shown in FIG. 8 as a function of photon energy and a peak at 100 keV for this particular configuration (1-cm thick Al sample and 1-mm thick CsI detector). The optimum tube voltage for generating such photons is 200-300 kV. For thicker samples, the optimum photon energy will increase (to minimize the attenuation), so higher energy sources may be required.

Returning to FIGS. 1 and 2, the x-ray source produces an x-ray beam 10, such as a conical x-ray beam. This beam is shaped into a sheet-like beam 12, for example, by passing through a slit collimator 8. The slit collimator 8 forms a sheet-like x-ray beam by blocking a portion of the beam and allowing a portion of the beam to pass through. In a specific case, the slit collimator 8 attenuates the blocked portion of the beam by at least a factor of 100. In other cases, different levels of attenuation may be used. Therefore, it is advantageous to fabricate it out of a high-Z material with high x-ray absorption, for example lead or tungsten. For example, for a 420-kV source, sufficient blockage can be achieved with either a 6.3-mm lead or 4.7-mm tungsten plate. Slit width impacts both signal intensity and system resolution. Widening the slit will improve the signal intensity (by letting more photons through) but will also reduce the system resolution. In a particular embodiment, the preferred slit width range is 0.2-3 mm.

In the illustrated embodiment, the slit collimator 8 has a thin rectangular profile so that the emitted beam 12 has a planar profile and a straight cross section. In particular, in the illustrated embodiment, the planar x-ray beam 12 is a planar fan beam after passing through slit collimator 8. However, other collimators 8 may be used with different profiles to produce a sheet-like beam 12 with any arbitrary curvilinear cross section. Any other non-planar sheet-like beam that samples a 2D subspace of the object's volume in a non-repetitive fashion could also be used, with appropriately modified algorithm for 3D data reconstruction. For example, such a non-planar beam can be generated by a slit having an arc, parabolic, or sine shape, with the axis of symmetry pointing towards the detector. The non-repetitive sampling requirement means that, during the image acquisition, each point of the detector should image no more than a single point of the object.

Figure 2B:
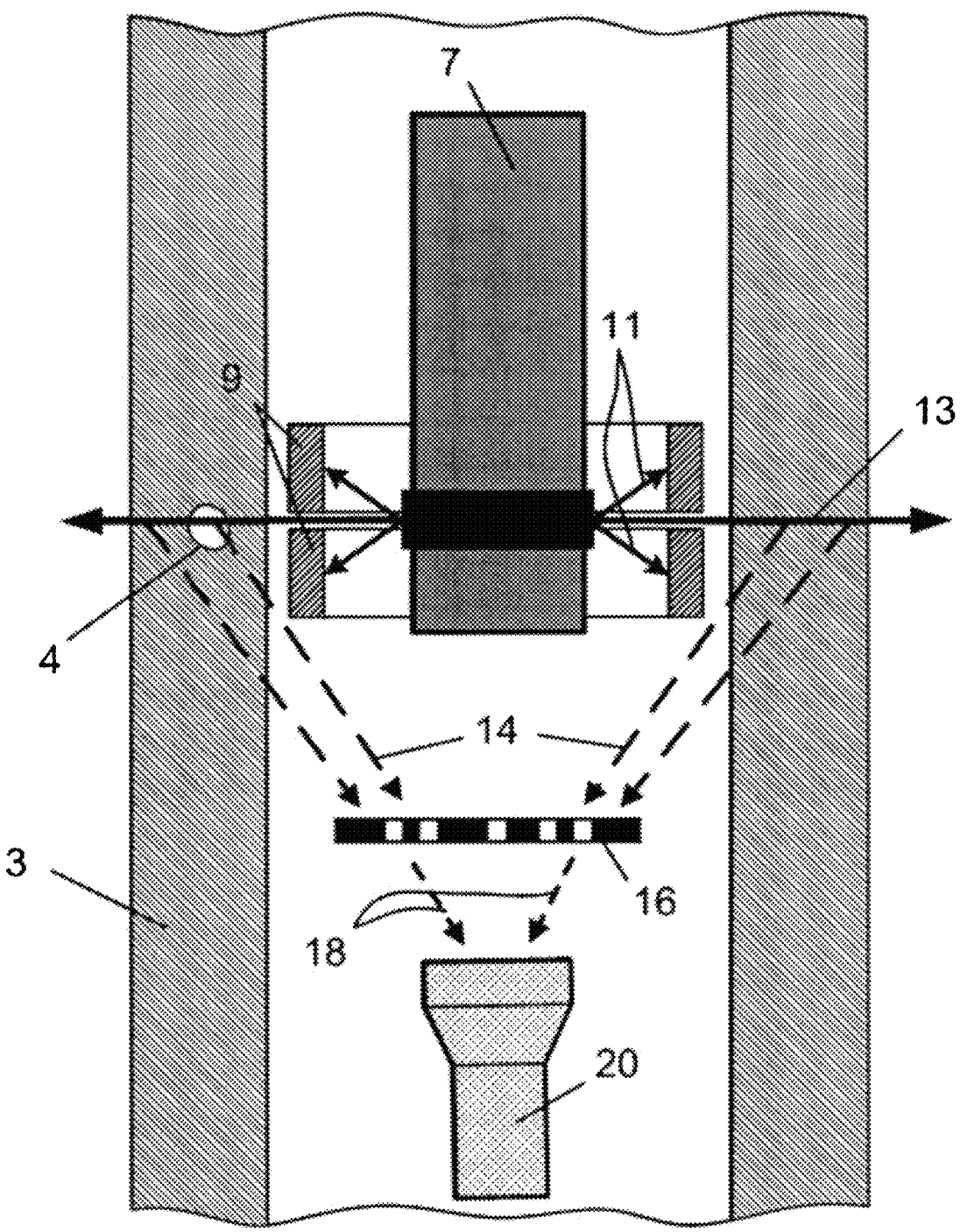
FIG. 2B is an alternative embodiment of the Compton tomography system, configured for internal scanning of objects with cylindrical symmetry.

FIG. 2B illustrates an embodiment of a Compton tomography system configured for 3D sampling of the walls of confined and hard-to-access spaces, in particular structures with cylindrical symmetry. For example, this could be the case for sections of pipelines and nuclear reactor components, which are completely inaccessible from the outside. In such embodiments, a panoramic x-ray source 7, which generates an output beam 11, symmetric with respect to the source's axis, can be used. In this case, the sheet-like beam 13 for irradiating the object 3 can be generated by utilizing a ring-shaped slit collimator 9 positioned around the circumference of the source. The camera 20 acquires ring-shaped slices of the object through an x-ray optical element 16. Object scanning can be performed by translating the source-camera assembly along the axis of the object.

Although FIGS. 1 and 2 demonstrate a system utilizing a single x-ray source, multiple sources can be disposed around the sample 2 to produce more uniform and intense irradiation. In some embodiments employing multiple sources the planar beams generated by each source overlap and are in the same plane.

The beam 12 irradiates a slice 11 of the sample 2. The irradiated slice 11 emits Compton-scattered x-ray photons 14. These photons are imaged by the x-ray camera 20. The camera 20 includes an x-ray optical element 16. The x-ray optics element 16 includes at least one apodized aperture 18. The apodized aperture 18 has a depth profile that is configured to provide a predetermined field of view (FOV), as described below. In the illustrated embodiment, the optics element 16 comprises an array of apodized apertures 18.

After passing through the optics element 16, the Compton-scattered x-rays 14 are imaged by the camera 20. X-ray camera 20 is any device capable of registering a 2D intensity distribution of incident x-rays on a planar surface. Such devices could include direct-detection semiconductor array (for low energies), scintillator-based flat-panel solid-state detectors, scintillator-based intensified x-ray cameras, Anger cameras, etc. In some embodiments, structured thick scintillators made of a high-Z material (such as columnar CsI), are used in such cameras for high-resolution detection of high-energy x-ray photons. The camera 20 may comprise a large area detector, for example a large array CMOS detector (also known as a flat-panel detector, or FPD) coupled to a scintillator. The camera 20 may also comprise a plurality of detectors. For example, the camera 20 may comprise tiled detectors, with a detector for each aperture 18 of the optics element 16.

The 3D imaging system presented in FIGS. 1 and 2, when used with a single imaging aperture, can be characterized by the following figure of merit (FOM), which is proportional to the square of the image signal-to-noise ratio (SNR):

$$Q = \frac{DQE\Delta^5 t}{d_1^2 \left(1 + \frac{W_0}{W_d}\right)^2}, \quad (8)$$

In the above Eq. (8), $W_d$ is the detector width, $W_0$ is the field of view, $d_1$ is the object distance from the imaging aperture, $\Delta$ is the spatial resolution, t is the signal integration time, and DQE—the detective quantum efficiency of the camera, which characterizes the noise properties of the camera (with DQE=1 being ideal). This expression for the system's FOM demonstrates that the image SNR improves when the detector's size $W_d$ increases. Therefore, it is advantageous to operate the system with as large detector as possible, although in practical situations there will be a trade-off with the detector cost and available physical space.

In further embodiments, a multi-imaging configuration is employed, in which a large detector is broken up into several (for simplicity, M×M, where M is an integer) sections, with each section recording the same object through multiple apertures. The images from each section are digitally added to reduce the noise. In these embodiments, the system is configured such that the images recorded in each section do not overlap with each other (for example, this can be achieved by applying an appropriate mask over the object to restrict its width). In this case, the FOM of each section is given by:

$$Q' = \frac{DQE\Delta^5 t}{d_1^2\left(1 + \frac{MW_0}{W_d}\right)^2} \quad (9)$$

During digital adding of the images from all sections of the detector, the signal increases by a factor of $M^2$ and the noise goes up by a factor of M, which means that the SNR increases by M, and FOM–by $M^2$. Therefore, the FOM of the sum image is:

$$Q = \frac{M^2 DQE\Delta^5 t}{d_1^2\left(1 + \frac{MW_0}{W_d}\right)^2}. \quad (10)$$

This is different from the FOM of a single-image system (Eq. 8) by a factor:

$$F = \left[\frac{M\left(1 + \frac{W_0}{W_d}\right)}{1 + \frac{MW_0}{W_d}}\right]^2 \quad (11)$$

FIG. 3 shows the enhancement factor F, for 15-cm and 29-cm FPDs (common commercially available sizes), compared to using the same detectors in a single-aperture configuration, as a function of the detector division factor. Clearly, the multiple-section imaging geometry is more advantageous: a significant additional FOM improvement, by a factor of up to 6-7, is possible, especially for the larger FPD.

When the system is implemented in a multi-imaging configuration the detector may be employed stereoscopically, which is illustrated in FIG. 3. In the multi-imaging configuration, cross sections of the sample 2 formed by the irradiating beam 12, are imaged through apertures 80 onto multiple imaging sections 60 of the detector without overlaps. In the simplest case, a single aperture is used to produces an image in each section 60, although an array of coded apertures can be used. Due to the large width of the detector 20, in comparison to the distance to the object 2, the imaged object cross section is viewed at different angles, depending on the position of the imaging sections 60 within the detector. If the cross section was infinitely thin, this stereoscopic effect would make very little difference because the image would remain independent of the viewing angle. However, if the width of the slice is finite (for example, several millimeters), as is usually chosen to achieve a compromise between the data acquisition speed and axial resolution, then stereoscopic effect may be employed for imaging purposes, especially if the in-plane resolution is higher then the beam width and the viewing angle variation is large (e.g, 50-60°).

The stereoscopic effect can be utilized to achieve partial suppression of attenuation artifacts. The described-below Compton tomography technique works best if the inspected structure is all made of lightweight, low-Z materials. The presence of high-Z, high-attenuation elements 70 generally results in artifacts, due to the attenuation of either the incident or Compton-scattered beam. These artifacts may reduce the ability to view a defect 4 behind such an absorbing element. When the defect is imaged at different angles, some of the directions may bypass the absorber 70, so the corresponding images will reveal the structure behind it (FIG. 5). By analyzing these multiple views and looking for changes in the shadows of the absorber, one can better determine if a particular dark spot is caused by an artifact or corresponds to an actual change in the material density.

Embodiments employing the stereographic effect may be used to perform a crude axial reconstruction in the acquired slices, i.e. to separate the features located in different sub-layers of the slice. As evident from FIG. 5, the mechanism of such reconstruction is similar to that of x-ray laminography (a reduced-angle version of tomography). In laminography, the detector measures the transmitted signal (in other words, it integrates the optical density) at various angles to the optical axis. In the described Compton tomography technique, each imaging zone 60 of the detector 20 integrates the scattered signal (proportional to physical density) at various angles to the optical axis. Therefore, the axial reconstruction can be performed with methods common in laminography, for example the Algebraic Reconstruction Technique (ART). The axial resolution $\delta_z$ provided by ART is estimated as:

$$\delta_z \approx \frac{\delta_x}{\sin\theta}, \quad (12)$$

where $\delta_x$ is the in-plane resolution, and σ—the maximum viewing angle counted from the optical axis (for σ=90°, when laminography becomes true tomography, the axial resolution equals in-plane resolution). If we use this as a guideline and assume $\delta_x$=1 mm and σ=30°, we end up with the axial resolution of $\delta_z$=2 mm.

Because the axial resolution is no longer constrained by the width of the beam 12, there is no need to compromise between the scanning speed and resolution. A fairly wide x-ray beam (that will irradiate a wide slice of the object and substantially improve the scanning speed due to the increased signal on the detector) may be used, which will not lose the axial resolution because it is defined only by the slice sub-layer reconstruction technique. The maximum practical beam width will depend on the number of the imaging zones 60 and the angular range of viewing (Eq. 12).

As illustrated, the Compton-scattered x-rays 14 originate from an irradiated slice 11 of the object 2. By translating the sample with respect to the Compton tomography system (which includes the x-ray source 6, slit collimator 8, apodized-aperture optics 16, and x-ray camera 20), or vice versa, images from multiple sample slices 11 can be acquired, until the whole sample volume 2 is scanned. Because individual images carry information about 2D electron density distribution within each slice 11, one can derive the information on the 3D sample structure by combining the data from multiple consecutive slices and performing appropriate data processing. Such processing may include 3D interpolation, contrast enhancement, gamma correction, deconvolution, filtering, artifact removal, etc.

In the illustrated embodiment, the direction of beam 12 is perpendicular to the optical axis of the x-ray camera 20. Accordingly, the irradiated slice 11 is parallel to the optics element 16. This provides a straightforward system configuration without perspective artifacts caused by tilt of the camera 20 with respect to the irradiated slice 11. However, in further embodiments, the camera 20 may be located at different angles with respect to the beam 12 and irradiated slice 11. In still further embodiments, the system may include multiple cameras 20, which can be disposed at various locations around the sample 2 for providing additional view or collecting more photons. In some cases, any image distortion created by off-angles may be corrected in image processing.

Additionally, in the illustrated embodiment, both the x-ray camera 20 and planar x-ray beam 12 are directed at 45 degrees to the surface (or the longest dimension) of the sample 2. This arrangement minimizes the beam attenuation on its way in and out of the sample and also provides a system configuration most amenable to slice-by-slice scanning, which is normally performed along the surface (or the longest dimension) of the sample 2, by displacing the sample 2 relative to the system or vice-versa. In some embodiments, the sample is placed on a linear translation stage for scanning. In other embodiments, the Compton tomography system is mounted on a movable robotic arm.

As discussed above, the optics system 16 includes one or more apertures 18. The aperture(s) may be formed in an x-ray absorbing plate. The x-ray absorbing plate may be made of various materials of various thicknesses to provide sufficient attenuation for system performance. To maximize the field of view, it is desirable to use aperture plates that are as thin as possible. The use of high-Z materials (such as tungsten, lead, gold, platinum) is preferred for fabricating these aperture plates. The imaging performance of a single aperture is relatively straightforward because it simply reproduces the object's intensity distribution in the detector's image plane. However, a single small aperture (small size is necessary for optimizing the resolution) will transmit only a small portion of the incident photons. Accordingly, some embodiments use multiple apertures for increasing the x-ray transmission. However, even for simple sources, the use of multiple apertures results in complicated multi-spot images, which necessitates special image processing to reconstruct the original object. In some embodiments, the aperture locations are chosen to facilitate the image reconstruction; such devices are also called coded apertures (CA).

Figure 9:
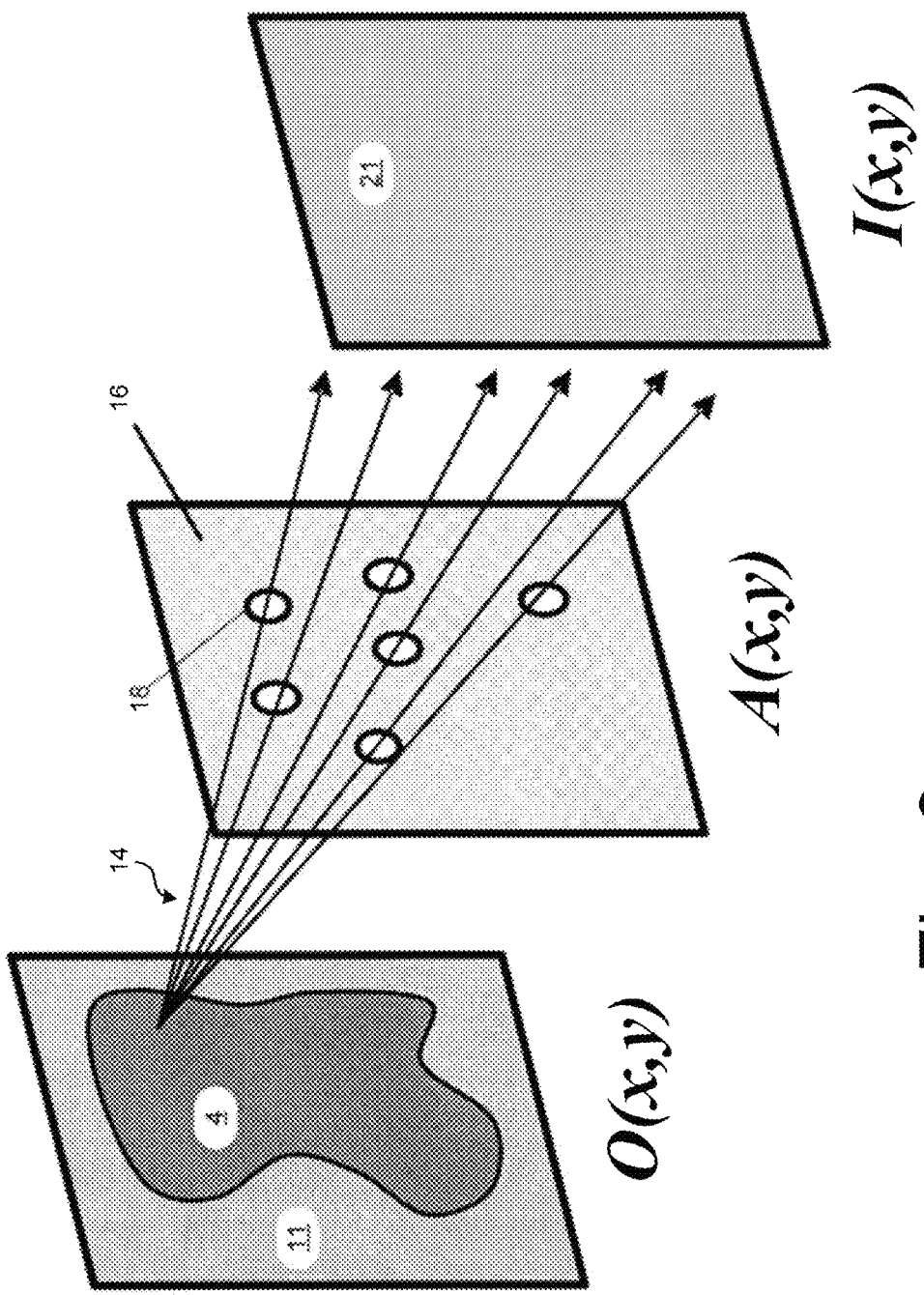
FIG. 9 is an illustration of imaging with a coded aperture optics.

FIG. 9 illustrates the imaging of a slice 11 including a defect 4 using an optical system 16 including an aperture array 18 to form an image 21. Each point source in an object with intensity distribution O(x,y) creates multiple spots in the image plane 21 I(x,y) upon passing through the CA 16 A(x,y), digitally represented as a set of "1"s and "0"s. The image intensity distribution I can be expressed as a convolution of the object matrix O and aperture matrix A, with some random noise term N added (to account for photon shot noise, camera noise, and other imperfections always present in the system):

$$I = O*A + N. \tag{13}$$

To reconstruct the original object O from its distorted image I, one can use another matrix G such that its correlation with A is a delta-function:

$$A \times G = \delta. \tag{14}$$

Then, $$I \times G = (O*A) \times G + N \times G = O*(A \times G) + N \times G = O + N \times G. \tag{15}$$

Therefore, the correlation of the image I with matrix G gives the original object O, with the addition of a noisy background N×G, which in most cases is fairly uniform and so can be subtracted. The key to realizing this image reconstruction process is finding such a CA profile A, for which a correlation matrix G, satisfying Eq. (14), exists.

Figure 10:
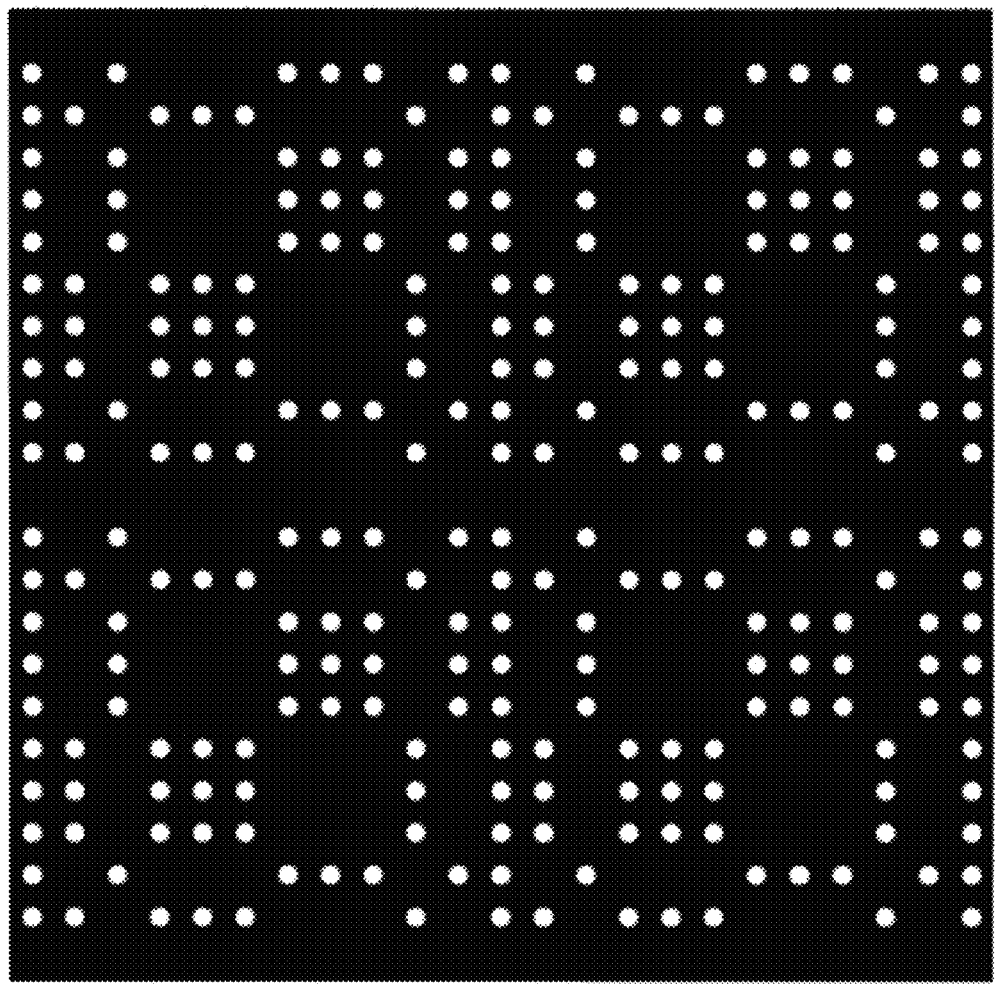
FIG. 10 is an example of a layout of a 23×23 apodized aperture array for the Compton tomography system of FIG. 1, based on a modified uniform redundant array (MURA) pattern.

Many suitable CA configurations are known in the art (See, e.g., R. Accorsi, "Design of Near-Field CA Imaging for High-resolution Medical and Industrial Gamma-ray Imaging, MIT Ph.D. Thesis at, 2001, (the portions of which describing CA configurations are hereby incorporated)). Randomly distributed apertures, despite their simplicity and only approximate agreement with Eq. (14), show relatively good performance. However, better signal-to-noise ratio (SNR) is achieved by using CAs based on uniform redundant arrays (URAs) and modified uniform redundant arrays (MURA), which exactly satisfy Eq. (14), with the correlation matrix being the CA itself (G=A). MURA patterns are more practical for fabrication because they allow making square arrays, whereas URA patterns always have unequal sides, although both may be employed in embodiments of the invention. An example of such a 23×23 MURA CA array is shown in FIG. 10. Here, dark area represents the x-ray absorbing material, and white circles—apertures produced in it.

However, conventional CA arrays, based on straight (cylindrical or rectangular) aperture, are not well suited for Compton tomography applications because of their small acceptance angle: complete transmission blockage due to aperture obscuration will occur at off-axis angle equal to d/T, and significant degradation will occur at an angle ~0.2 d/T where d is the aperture diameter, and T-plate thickness. For example, for a 0.5-mm aperture fabricated in a 6-mm plate, the onset of transmission distortions will happen at off-axis angle of ~1 degree. Such distortions cause only minor effects on the image when a single aperture is used (a typical result would be the reduction of image intensity on the periphery, known as vignetting) but they are much more serious in CA systems. Such distortions effectively modify the transmission function of the CA, which causes noise, distortions, and artifacts to appear in the reconstructed images.

The problem of the small acceptance angle is solved by apodized-aperture x-ray imaging optics, which has been already partially described in U.S. Pat. No. 8,705,694, entitled "X-Ray Imaging System And Method," filed Nov. 23, 2009, which is incorporated by reference in its entirety. An aperture with a depth-dependent profile (apodization) having the smallest diameter in the center of the plate and gradually opening towards the surfaces, achieves a combination of high-resolution and wide field of view due to greatly reduced aperture obscuration. It was shown that apertures with Gaussian and Lorentzian apodizations achieve 4-5 times wider field of view compared to a cylindrical aperture of the same spatial resolution. Such apodized apertures can be fabricated by precise 3D laser processing. Alternatively, good approximations to ideal smooth apodizations can be produced by stacking multiple sheets with conventional cylindrical apertures of various diameters.

Figure 11:
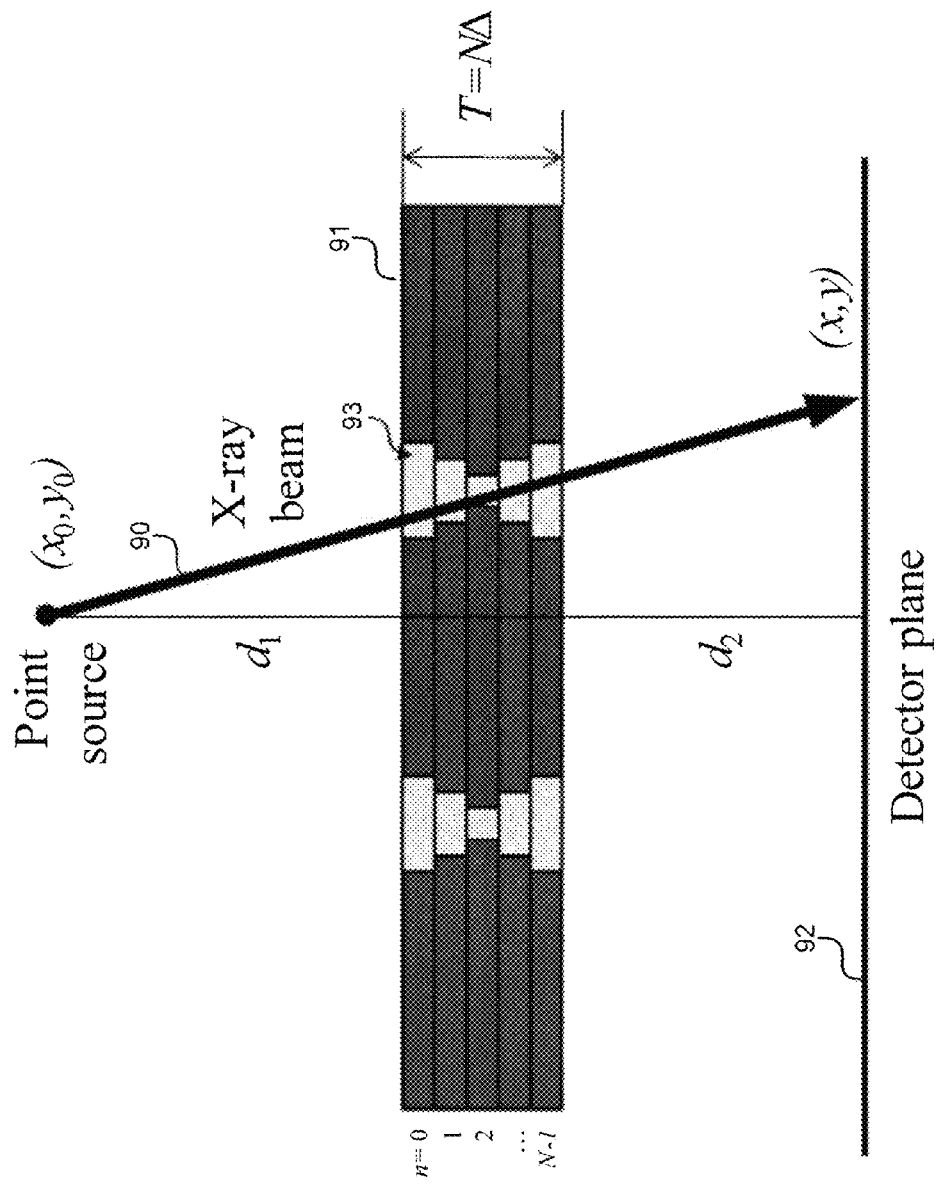
FIG. 11 is an illustration of a multilayer coded aperture.

FIG. 11 illustrates an apodized aperture array 91 formed by stacking multiple sheets, n, having cylindrical apertures of various diameters to approximate a smooth apodization. The layers are sufficiently thin, such that the effects of obscuration and incomplete absorption in each layer can be neglected. Here, a point source $(x_0, y_0)$ produces an X-ray beam 90 that impinges detector plane 92 at a point (x,y). A technique for modeling apodized CA imaging is presented below with respect to this figure. In this case, the behavior of each layer can be modeled through conventional CA approaches, and the PSF of the whole CA can be calculated as a product of the attenuations of individual layers:

$$I(x, y) = \exp\left[-\sum_{n=0}^{N-1} \alpha_n\left(x_0 + (x-x_0)\frac{d_1 + n\Delta}{d_1 + T + d_2}, y_0 + (y-y_0)\frac{d_1 + n\Delta}{d_1 + T + d_2}\right)\right], \quad (16)$$

where x and y are the coordinates in the detector plane, $d_1$ and $d_2$—source-CA and CA-detector distances, $\Delta$—individual layer thickness, T—total structure thickness, and the attenuation profiles of individual layers $\alpha_n$ are binary functions:

$$\alpha_n(x, y) = \begin{bmatrix} \frac{\alpha_{max}}{N}, & \text{solid area} \\ 0, & \text{aperture} \end{bmatrix}. \quad (17)$$

Figure 12:
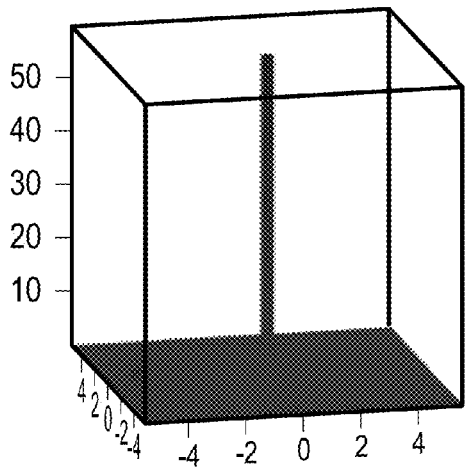
FIG. 12 shows the results of simulation for a 23×23 MURA coded aperture, which compares the performance of a cylindrical aperture array with that of an apodized aperture array.
Figure 12:
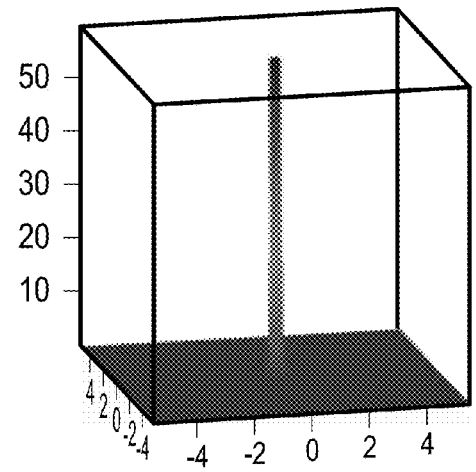
Figure 12:
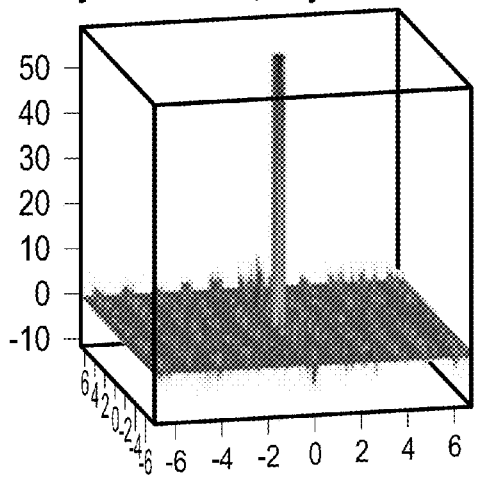
Figure 12:
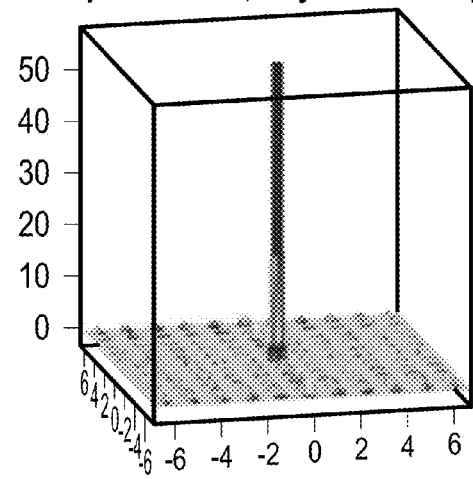
Figure 12:
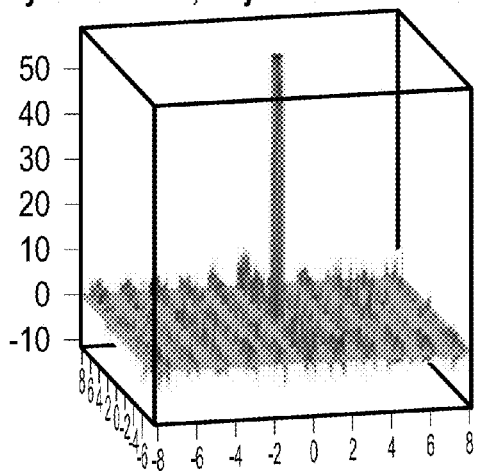
Figure 12:
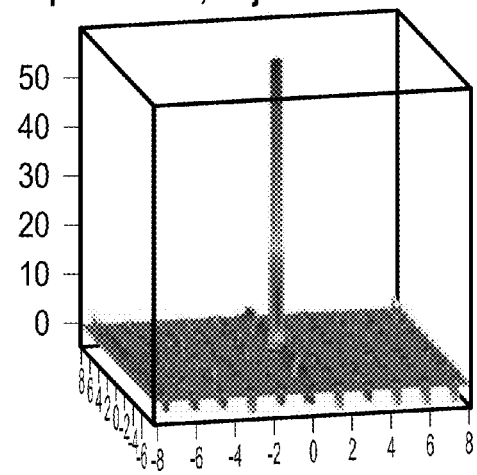

FIG. 12 shows the results of simulation for a CA geometry having the 23×23 aperture MURA pattern illustrated in FIG. 10 with 5 layers, aperture spacing 1 mm, optical density $\alpha_{max}=5$, and CA thickness T=3.2 mm. Two different CA geometries were compared: 1) a CA composed of cylindrical apertures (5 identical layers) having a diameter of 0.45 mm; and 2) an apodized CA with aperture diameters of 0.7, 0.5, 0.4, 0.5, and 0.7 mm in its 5 layers. The dimensions of the both CA's were chosen to produce identical FWHM of PSF (so that their resolutions are the same). The CA-detector distance d2 was fixed at 100 mm but the source-CA distance d1 was varied from infinity down to 200 mm.

The simulations show that, as $d_1$ decreases, the distortions of the CA coding/decoding performance become more pronounced due to the increased x-ray angle of incidence with respect to the CA optical axis, which results in partial aperture obscuration on the image periphery. However, the apodized CA is clearly much more resilient to this effect than the cylindrical CA: it achieves up to 3 times lower noise at the same distance to the source, compared to the cylindrical CA.

Figure 13:
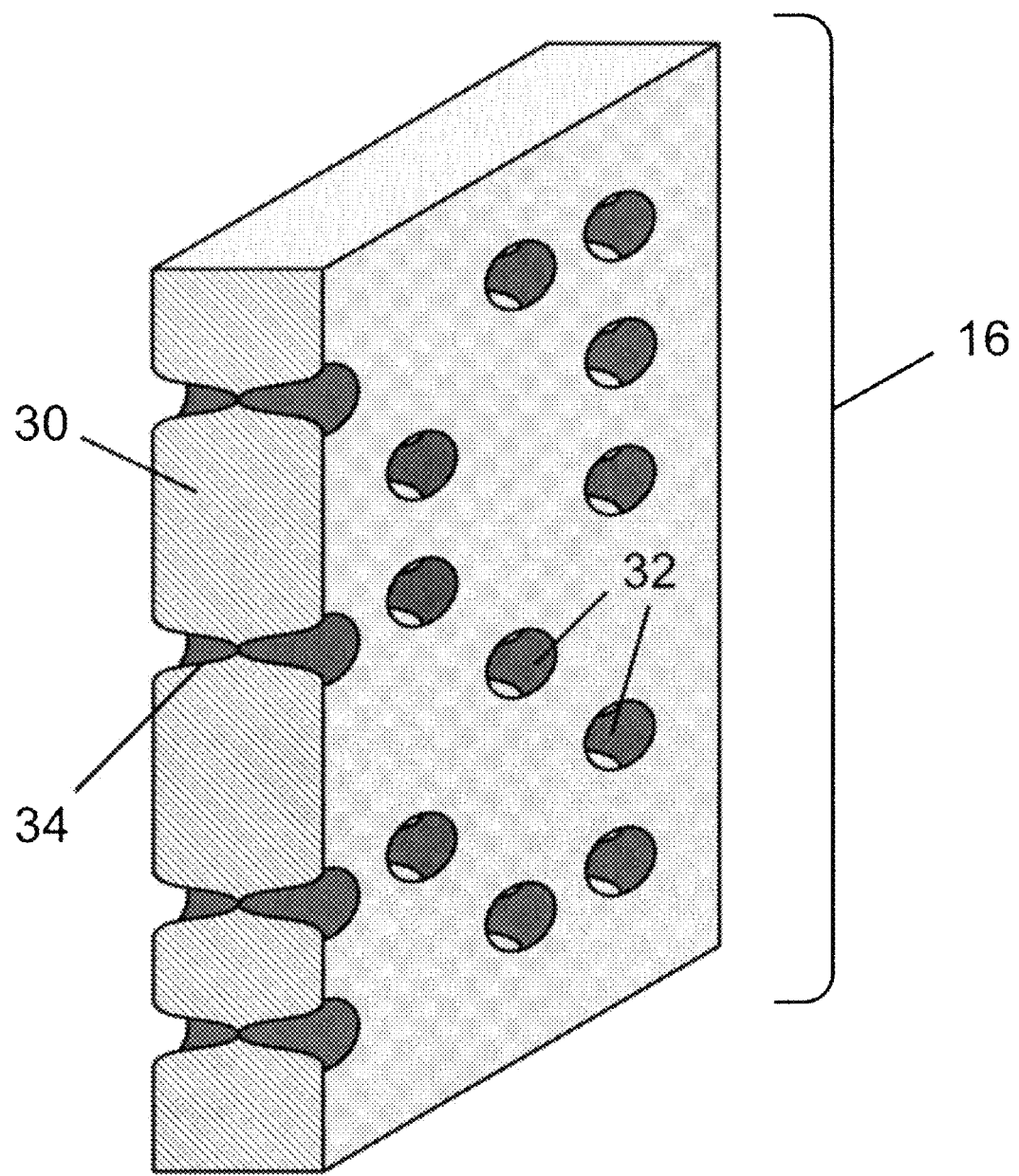
FIG. 13 is a perspective view of an apodized-aperture x-ray imaging optics used in a Compton tomography system of FIGS. 1 and 2.

FIG. 13 illustrates another example of an x-ray optics element 16 comprising an x-ray absorbing plate 30 having apodized apertures 32. In this example, the apertures have a smooth apodization depth dependent profile 34. The depth dependent profile is symmetric about the midplane of the thickness of the optics element 16. Various smooth profiles may be used, for example, the apertures may have Lorentzian or Gaussian profiles in one of the regions of symmetry. In such a case, the apertures have two Lorentzian or two Gaussian profiles joined at their respective maxima.

In various embodiments, the specific depth dependent profiles utilized may be selected based on various criteria. For example, the depth dependent profiles may be selected to optimize the imaging performance based on the system parameters, which may include: x-ray photon energy, attenuation coefficient, plate thickness, spatial resolution, and field of view. The distribution of the apertures 32 in the plate 30 is determined by the selected type of the coded aperture, for example a MURA array similar to the one shown in FIG. 10

Figure 14:
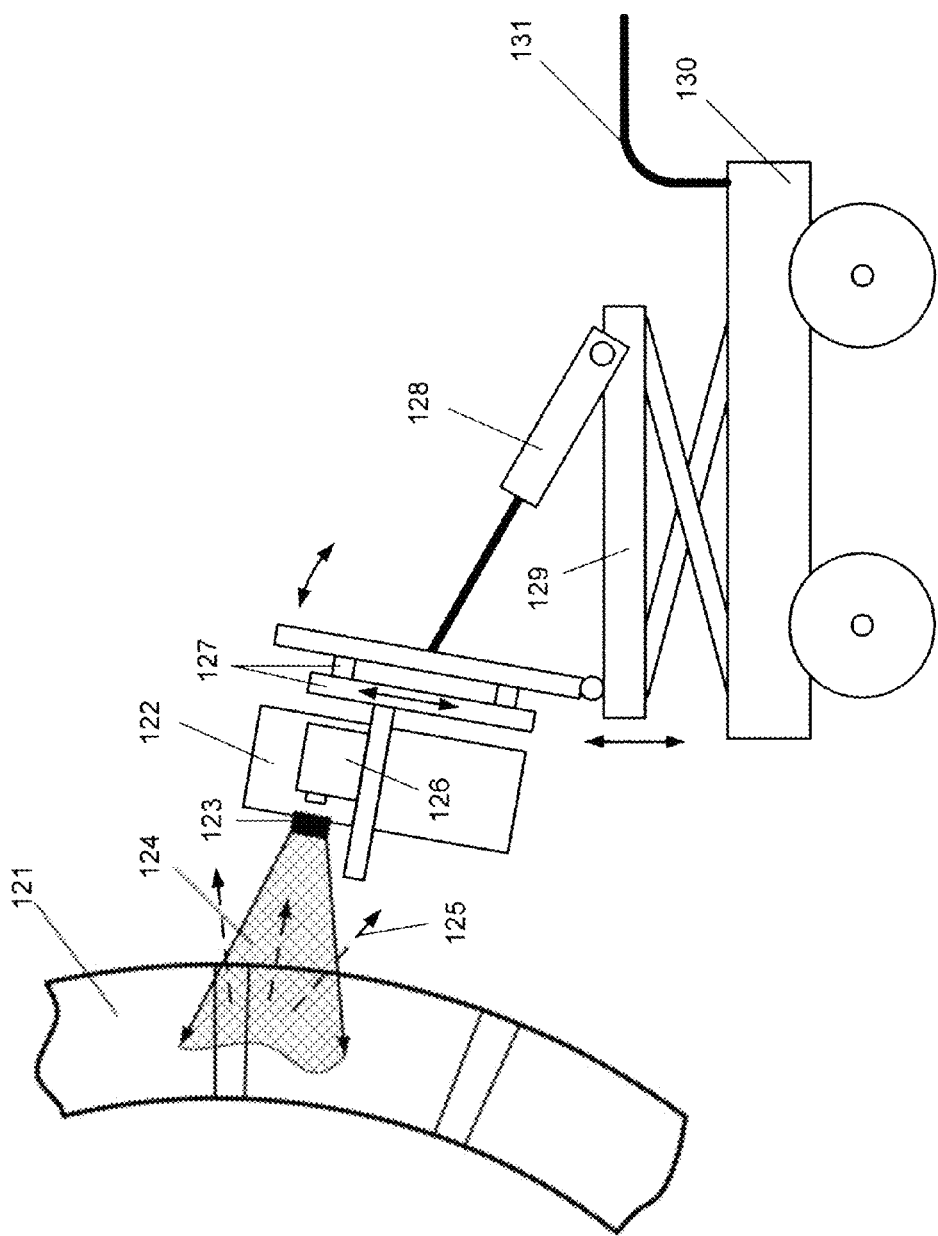
FIG. 14 is an illustration of a mobile Compton tomography system.

As discussed above, the slice-by-slice acquisition can be accomplished by translating the sample or by translating the Compton tomography system. FIG. 14 illustrates a mobile Compton tomography system where multiple slice image acquisition is accomplished by translating the Compton tomography system. Sample 121 is the object being imaged, which may comprise a component or device under inspection. The system comprises an x-ray source 122 configured to generate an x-ray beam. A slit collimator 123 shapes the beam to form a planar X-ray fan beam 124. The fan beam 124 irradiates a slice of the component under test 121, producing Compton-scattered x-rays 125. The system further comprises an x-ray camera and imaging optics 126. The x-ray camera 126 and x-ray source 122 are co-mounted on a translation stage 127 configured to translate the camera 126 and source 122 in the x and y directions. The translation stage 127 is coupled to a tilt controlling actuator 128 and a lift table 129. The lift table 129 is mounted on a motorized cart 130 allowing the system to move. A power and control line 131 provides I/O and power to the system. For example, the line 131 may be coupled to a control system configured to control operation of the system and provide image processing on images received from camera 126.

These embodiments of a Compton tomography system also solves another important challenge of CA imaging systems, which complicates their practical utilization, namely imaging 3D structures. The image reconstruction algorithm presented in Eqs. (14) and (15), works only when the object is located at a fixed distance from the CA, or essentially, within a plane at a certain distance from the CA. Out-of-plane objects cannot be reconstructed in this case, and will produce image artifacts. The system design shown in FIGS. 1 and 2 effectively eliminates this problem by irradiating a single planar slice of the sample at a time.

Some embodiments of a Compton tomography system use a unique method of reconstructing 3D object structure from the raw slice data. Because the raw data is acquired in parallel slices (sample cross sections), the reconstruction technique is different from Radon transform used in conventional Computed Tomography (CT). The 3D structure reconstruction technique described below is less computationally intensive than Radon transform and so is less likely to introduce image artifacts. It works for any arbitrary set of parallel object cross sections and for arbitrary position and orientation of the detector. In additional embodiments, this reconstruction technique can be used with other data acquisition methods that allows collecting images of object's internal structure via parallel 2D cross sections.

Figure 15:
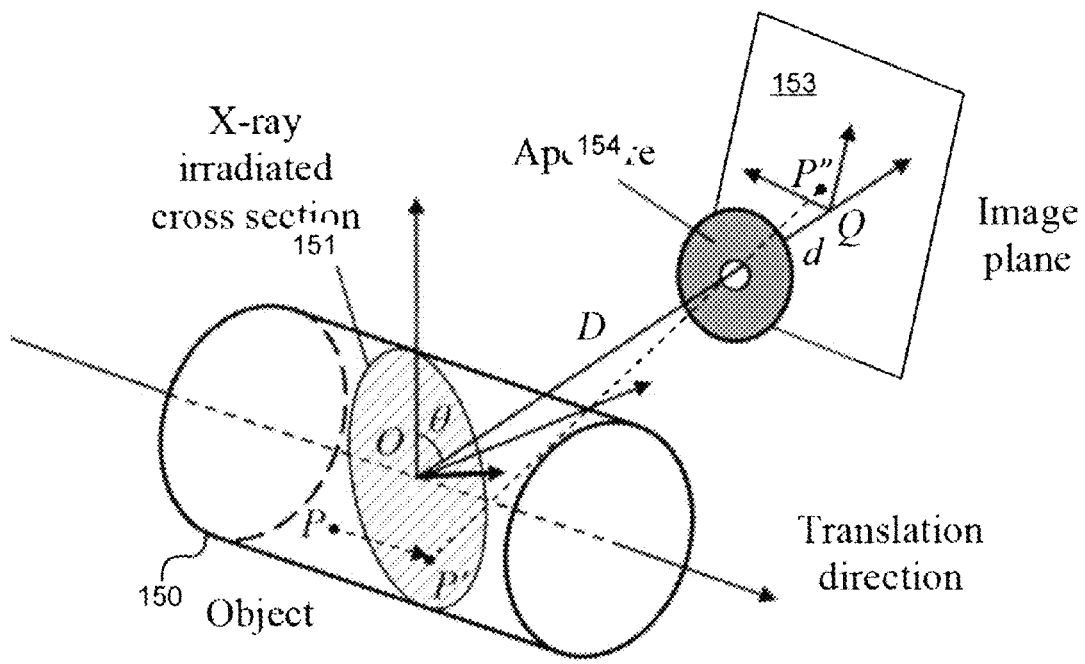
FIG. 15 is an illustration of an explanatory geometry for an algorithm for tomographic reconstruction based on a series of cross sections.

The general geometry of the considered imaging system is shown in FIG. 15. The object 150 (assumed to be a cylinder for simplicity) is irradiated 151 by a planar x-ray beam with normal vector $\vec{n}$. The Compton scattered x-rays pass through an aperture 154 and form an image on image plane 153. The O2 coordinate system is a fixed laboratory reference frame chosen as follows: z-axis is the direction of the object translation during scanning (it is normally parallel to the horizontal plane), y-axis is vertical direction, and x-direction completes the orthonormal basis ($\hat{x}=\hat{y}\times\hat{z}$). The center of the coordinate system O is the intersection between the camera 153 axis vector $\vec{v}$ and the X-ray plane 151. For the Qϵn image plane system, unit vector $\vec{\epsilon}$ is chosen to be perpendicular to $\vec{y}$:

$$\hat{\xi} = \frac{\hat{y}\times\vec{v}}{|\hat{y}\times\vec{v}|}, \quad \hat{\eta} = \vec{v}\times\hat{\xi} = \frac{\hat{y} - \vec{v}(\hat{y}\cdot\vec{v})}{|\hat{y}\times\vec{v}|}. \quad (18)$$

Reconstructing the 3D object structure from a set of cross sectional frames may comprise solving two major problems: First, (For an arbitrary point inside the object P(x, y, z), how to identify the frame (slice) number j, which contained the information about this point? Second, (B). Given a particular frame j, how to locate point P (or a point closest to it) within the image?

The answer to Problem A is relatively straightforward. After each frame is taken, the object is displaced by distance Δ in z-direction. Therefore, when frame j is imaged, point P is at a new position P' given by:

$$\overrightarrow{QP'} = \overrightarrow{QP} + j\Delta \vec{z}. \tag{19}$$

If this new position lies in the X-ray plane, it has to satisfy the following condition:

$$\overrightarrow{OP'} \cdot \vec{n} = 0. \tag{20}$$

From here, we can calculate the frame number that contains point P:

$$j = -\frac{1}{\Delta} \frac{(\overrightarrow{OP} \cdot \vec{n})}{(\vec{n} \cdot \hat{z})}. \tag{21}$$

The location of point P after translation into the X-ray plane is:

$$\overrightarrow{OP'} = \overrightarrow{OP} - \frac{(\overrightarrow{OP} \cdot \vec{n})}{(\vec{n} \cdot \hat{z})}\hat{z} \tag{22}$$

Figure 16:
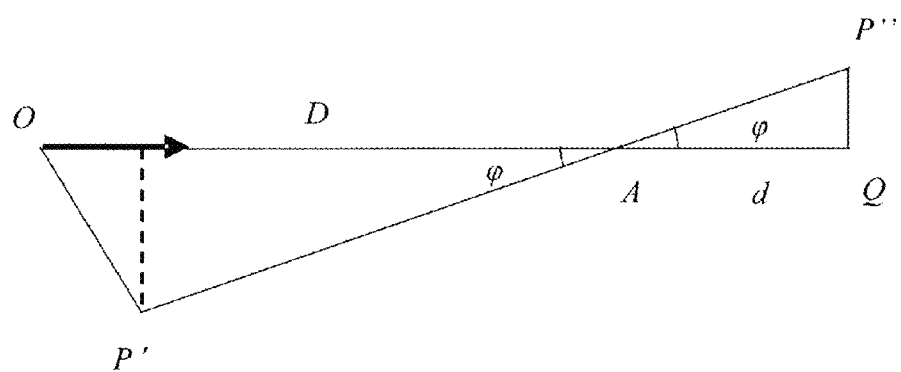
FIG. 16 is an illustration of a plane of FIG. 15 for explanation of the algorithm for tomographic reconstruction.

The solution to Problem B involves both the position of the X-ray plane with respect to the object and the orientation of the camera with respect to the X-ray plane. First, we need to find the location of point P'', the image of P', within the image plane. Then, we have to calculate the coordinates of P'' in terms of ϵ and η. For the sake of explanation, the calculation of P'' position is considered only the plane OP'P''Q (FIG. 16):

$$\overrightarrow{OA} = D\vec{v}, \overrightarrow{AQ} = d\vec{v} \tag{23}$$

$$\overrightarrow{OP''} = \overrightarrow{AP''} - \overrightarrow{AQ} =$$

$$\frac{\overrightarrow{P'A}}{|\overrightarrow{P'A}|} \frac{d}{\cos\varphi} - d\vec{v} = \frac{d|\overrightarrow{OA}|}{(\overrightarrow{OA} \cdot \overrightarrow{P'A})}\overrightarrow{P'A} - d\vec{v} = \frac{d}{(\overrightarrow{P'A} \cdot \vec{v})}\overrightarrow{P'A} - d\vec{v}$$

$$\overrightarrow{QP''} = \frac{d(D\vec{v} - \overrightarrow{OP'})}{(D\vec{v} - \overrightarrow{OP'}) \cdot \vec{v}} - d\vec{v} =$$

$$\frac{d(D\vec{v} - \overrightarrow{OP'}) - [D - (\overrightarrow{OP'} \cdot \vec{v})]d\vec{v}}{D - (\overrightarrow{OP'} \cdot \vec{v})} = d\frac{(\overrightarrow{OP'} \cdot \vec{v})\vec{v} - \overrightarrow{OP'}}{D - (\overrightarrow{OP'} \cdot \vec{v})}$$

Finally, the coordinates of point P'' in the image coordinate system are:

$$\xi = \overrightarrow{QP''} \cdot \hat{\xi} = \overrightarrow{QP''} \cdot \frac{(\hat{y} \times \hat{v})}{|\hat{y} \times \hat{v}|} = \tag{24a}$$

$$d\frac{(\overrightarrow{OP'} \cdot \vec{v})\vec{v} - \overrightarrow{OP'}}{D - (\overrightarrow{OP'} \cdot \vec{v})} \cdot \frac{(\hat{y} \times \hat{v})}{|\hat{y} \times \hat{v}|} = -d\frac{(\overrightarrow{OP'} \cdot \hat{x})(\hat{v} \cdot \hat{z}) - (\overrightarrow{OP'} \cdot \hat{z})(\hat{v} \cdot \hat{x})}{[D - (\overrightarrow{OP'} \cdot \vec{v})]|\hat{y} \times \hat{v}|}$$

$$\eta = \overrightarrow{QP''} \cdot \hat{\eta} = \tag{24b}$$

$$d\frac{[(\overrightarrow{OP'} \cdot \vec{v})\vec{v} - \overrightarrow{OP'}]}{D - (\overrightarrow{OP'} \cdot \vec{v})} \cdot \frac{[\hat{y} - \vec{v}(\hat{y} \cdot \vec{v})]}{|\hat{y} \times \vec{v}|} = d\frac{(\overrightarrow{OP'} \cdot \vec{v})(\hat{y} \cdot \vec{v}) - (\overrightarrow{OP'} \cdot \hat{y})}{[D - (\overrightarrow{OP'} \cdot \vec{v})]|\hat{y} \times \vec{v}|}$$

Eqs. (24) are the most general solutions of Problem B in vector form. For real-world computation, it may be more convenient to express the solution in terms of the coordinates x, y, z and angle θ between vectors $\vec{y}$ and $\vec{v}$:

$$\text{Frame number: } j = -\frac{1}{\Delta}\left(\frac{xn_x + yn_y}{n_z} + z\right) \tag{25a}$$

$$\overrightarrow{OP'} = (x, y, z), z' = -\frac{xn_x + yn_y}{n_z}$$

$$\overrightarrow{OP'} \cdot \vec{v} = xv_x + yv_y + z'v_z$$

$$\hat{y} \times \vec{v} = \sin\theta, \hat{y} \cdot \vec{v} = \cos\theta$$

$$\xi = -d\frac{xv_z - z'v_x}{[D - (xv_x + yv_y + z'v_z)]|\sin\theta|} \tag{25b}$$

$$\eta = -d\frac{y - (xv_x + yv_y + z'v_z)\cos\theta}{[D - (xv_x + yv_y + z'v_z)]|\sin\theta|} \tag{25c}$$

Eqs. (25b,c) simplify significantly in an important special case when the camera axis is perpendicular to the X-ray plane ($\vec{n} = \vec{v}$):

$$\xi = -\frac{d}{D|\sin\theta|}(xv_z - z'v_x) \tag{21a}$$

$$\eta = -\frac{d}{D|\sin\theta|}y \tag{21b}$$

To summarize, an algorithm for 3D object reconstruction according to one embodiment is as follows. For any point P(x, y, z) (here the coordinates are measured with respect to the initial position of the object, before the scanning started), the frame number j, in which this point was recorded, is first located according to Eq. (20a). Next, Eqs. (20b,c) are used to find the exact location within frame j where point P was recorded. By cycling through all possible values of x, y, z coordinates, the whole object may be reconstructed.

Some advantages of some embodiments of the present invention include: capability for 3D object structure acquisition, operation in a one-sided configuration amenable to scanning large objects, quick data acquisition due to 2D (as opposed to point-by-point) sample irradiation and efficient signal collection with an apodized coded-aperture optics, compactness, and high-contrast imaging in both low-Z and high-Z materials. Certain embodiments of the invention can be used in the fields of non-destructive testing and evaluation and medical imaging.

Figure 17:
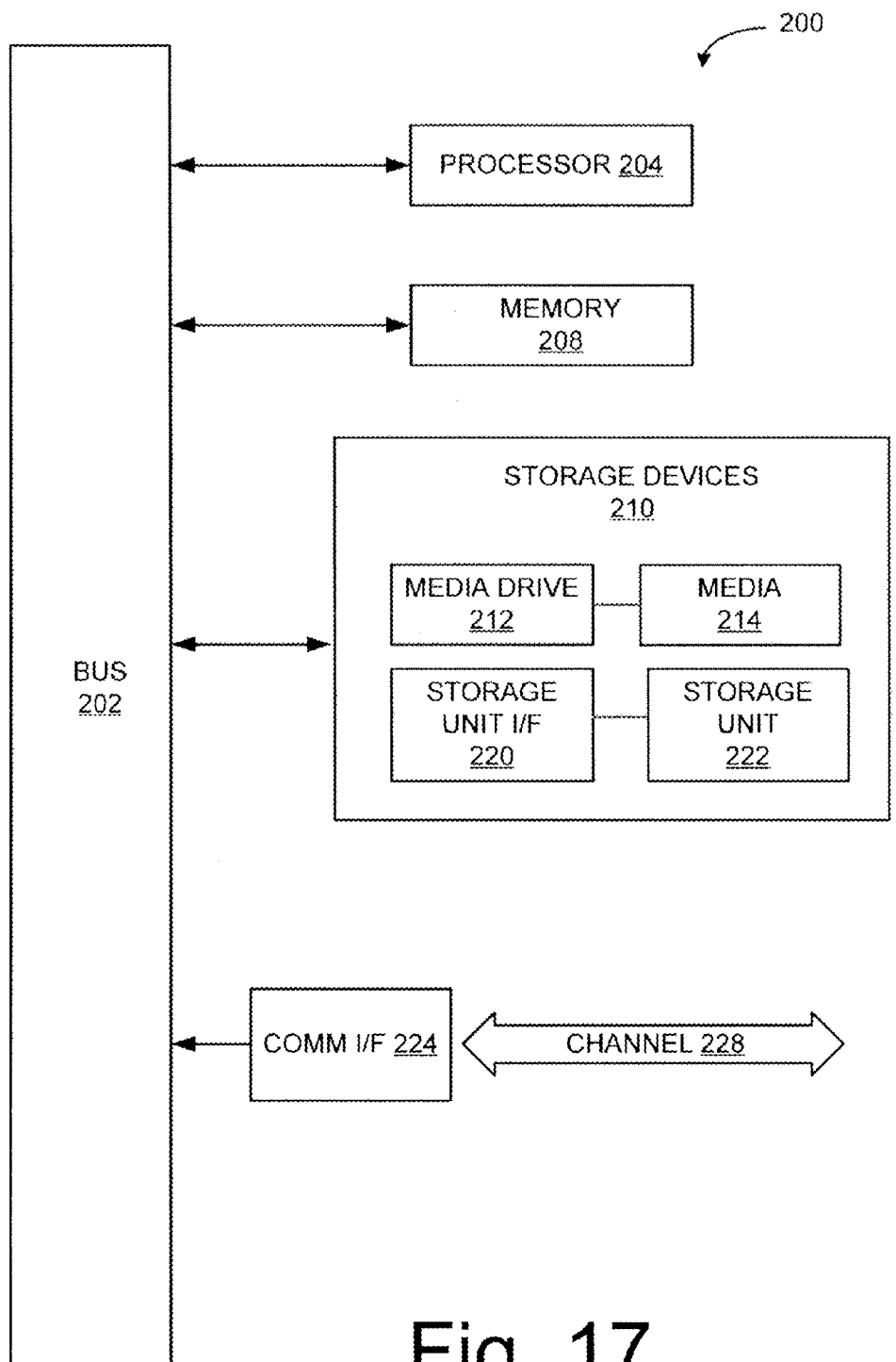
FIG. 17 is an illustration of an example computing module that may be used in implementing various features of embodiments of the invention.

As used herein, the term module might describe a given unit of functionality that can be performed in accordance with one or more embodiments of the present invention. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. In implementation, the various modules described herein might be implemented as discrete modules or the functions and features described can be shared in part or in total among one or more modules. In other words, as would be apparent to one of ordinary skill in the art after reading this description, the various features and functionality described herein may be implemented in any given application and can be implemented in one or more separate or shared modules in various combinations and permutations. Even though various features or elements of functionality may be individually described or claimed as separate modules, one of ordinary skill in the art will understand that these features and functionality can be shared among one or more common software and hardware elements, and such description shall not require or imply that separate hardware or software components are used to implement such features or functionality.

Where components or modules of the invention are implemented in whole or in part using software, in one embodiment, these software elements can be implemented to operate with a computing or processing module capable of carrying out the functionality described with respect thereto. One such example computing module is shown in FIG. 17. Various embodiments are described in terms of this example-computing module 200. After reading this description, it will become apparent to a person skilled in the relevant art how to implement the invention using other computing modules or architectures.

Referring now to FIG. 17, computing module 200 may represent, for example, computing or processing capabilities found within desktop, laptop and notebook computers; handheld computing devices (PDA's, smart phones, cell phones, palmtops, etc.); mainframes, supercomputers, workstations or servers; or any other type of special-purpose or general-purpose computing devices as may be desirable or appropriate for a given application or environment. Computing module 200 might also represent computing capabilities embedded within or otherwise available to a given device. For example, a computing module might be found in other electronic devices such as, for example, digital cameras, navigation systems, cellular telephones, portable computing devices, modems, routers, WAPs, terminals and other electronic devices that might include some form of processing capability.

Computing module 200 might include, for example, one or more processors, controllers, control modules, or other processing devices, such as a processor 204. Processor 204 might be implemented using a general-purpose or special-purpose processing engine such as, for example, a microprocessor, controller, or other control logic. In the illustrated example, processor 204 is connected to a bus 202, although any communication medium can be used to facilitate interaction with other components of computing module 200 or to communicate externally.

Computing module 200 might also include one or more memory modules, simply referred to herein as main memory 208. For example, preferably random access memory (RAM) or other dynamic memory, might be used for storing information and instructions to be executed by processor 204. Main memory 208 might also be used for storing temporary variables or other intermediate information during execution of instructions to be executed by processor 204. Computing module 200 might likewise include a read only memory ("ROM") or other static storage device coupled to bus 202 for storing static information and instructions for processor 204.

The computing module 200 might also include one or more various forms of information storage mechanism 210, which might include, for example, a media drive 212 and a storage unit interface 220. The media drive 212 might include a drive or other mechanism to support fixed or removable storage media 214. For example, a hard disk drive, a floppy disk drive, a magnetic tape drive, an optical disk drive, a CD or DVD drive (R or RW), or other removable or fixed media drive might be provided. Accordingly, storage media 214 might include, for example, a hard disk, a floppy disk, magnetic tape, cartridge, optical disk, a CD or DVD, or other fixed or removable medium that is read by, written to or accessed by media drive 212. As these examples illustrate, the storage media 214 can include a computer usable storage medium having stored therein computer software or data.

In alternative embodiments, information storage mechanism 210 might include other similar instrumentalities for allowing computer programs or other instructions or data to be loaded into computing module 200. Such instrumentalities might include, for example, a fixed or removable storage unit 222 and an interface 220. Examples of such storage units 222 and interfaces 220 can include a program cartridge and cartridge interface, a removable memory (for example, a flash memory or other removable memory module) and memory slot, a PCMCIA slot and card, and other fixed or removable storage units 222 and interfaces 220 that allow software and data to be transferred from the storage unit 222 to computing module 200.

Computing module 200 might also include a communications interface 224. Communications interface 224 might be used to allow software and data to be transferred between computing module 200 and external devices. Examples of communications interface 224 might include a modem or softmodem, a network interface (such as an Ethernet, network interface card, WiMedia, IEEE 802.XX or other interface), a communications port (such as for example, a USB port, IR port, RS232 port Bluetooth® interface, or other port), or other communications interface. Software and data transferred via communications interface 224 might typically be carried on signals, which can be electronic, electromagnetic (which includes optical) or other signals capable of being exchanged by a given communications interface 224. These signals might be provided to communications interface 224 via a channel 228. This channel 228 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to media such as, for example, memory 208, storage unit 220, media 214, and channel 228. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing module 200 to perform features or functions of the present invention as discussed herein.

While various embodiments of the present invention have been described above, it should be understood that they have been presented by way of example only, and not of limitation. Likewise, the various diagrams may depict an example architectural or other configuration for the invention, which is done to aid in understanding the features and functionality that can be included in the invention. The invention is not restricted to the illustrated example architectures or configurations, but the desired features can be implemented using a variety of alternative architectures and configurations. Indeed, it will be apparent to one of skill in the art how alternative functional, logical or physical partitioning and configurations can be implemented to implement the desired features of the present invention. Also, a multitude of different constituent module names other than those depicted herein can be applied to the various partitions. Additionally, with regard to flow diagrams, operational descriptions and method claims, the order in which the steps are presented herein shall not mandate that various embodiments be implemented to perform the recited functionality in the same order unless the context dictates otherwise.

Although the invention is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the invention, whether or not such embodiments are described and whether or not such features are presented as being a part of a described embodiment. Thus, the breadth and scope of the present invention should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "module" does not imply that the components or functionality described or claimed as part of the module are all configured in a common package. Indeed, any or all of the various components of a module, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

The invention claimed is:

1. A Compton tomography system for three-dimensional object characterization, comprising:
    an x-ray source to emit an x-ray beam;
    a collimator disposed to collimate the x-ray beam into a sheet-like x-ray beam for irradiating a predetermined two-dimensional subset of the object;
    an x-ray optical element comprising an aperture, having a first surface and a second surface, disposed to receive x-rays produced by Compton scattering of at least a portion of the sheet-like x-ray beam from an object, the aperture having a depth-dependent profile wherein an outer diameter of the aperture at the first surface and the second surface is larger than an inner diameter at a center of the aperture;
    an x-ray camera disposed to image x-ray photons transmitted by the x-ray optical element and to acquire the resulting images;
    a scanning arrangement to enable the irradiation and imaging a plurality of two-dimensional subsets of the object; and
    an image processor for combining the Compton-scattered images corresponding to the plurality of two-dimensional subsets of the object into a three-dimensional representation of the object.

2. The Compton tomography system of claim 1, wherein the sheet-like x-ray beam is a ring-shaped x-ray beam.

3. The Compton tomography system of claim 1, wherein the sheet-like x-ray beam is a planar x-ray beam.

4. The Compton tomography system of claim 3, wherein the x-ray optical element comprises an array of apertures, and the aperture is an element of the array of apertures, each aperture of the array having the predetermined depth profile.

5. The Compton tomography system of claim 4, wherein the x-ray camera records a separate image from each aperture of the array of apertures.

6. The Compton tomography system of claim 5, wherein the x-ray camera comprises a plurality of detectors, with each detector of the plurality disposed to capture an image from a corresponding aperture of the array of apertures.

7. The Compton tomography system of claim 5, wherein the x-ray camera comprises a single detector disposed to capture the plurality of separate images.

8. The Compton tomography system of claim 5, wherein the image processor is additionally configured to obtain the separate images from the x-ray camera to combine the separate images into a composite image.

9. The Compton tomography system of claim 4, wherein the aperture array is a coded aperture array.

10. The Compton tomography system of claim 9, wherein the coded aperture array is a uniform redundant array or a modified uniform redundant array.

11. The Compton tomography system of claim 3, wherein the normal vector of the collimator is perpendicular to the normal vector of the x-ray optical element.

12. The Compton tomography system of claim 3, further comprising a receptacle for receiving the object.

13. The Compton tomography system of claim 12, wherein the receptacle and collimator are configured such that the planar x-ray beam impinges at approximately a 45° angle to the longest axis of the object.

14. The Compton tomography system of claim 12, wherein the receptacle is configured to move with respect to the x-ray beam, x-ray optical element, and x-ray camera.

15. The Compton tomography system of claim 12, wherein the x-ray beam, x-ray optical element, and x-ray camera are configured to move with respect to the receptacle.

16. The Compton tomography system of claim 1, wherein the x-ray source comprises an x-ray tube, a linear accelerator, or a radioisotope source.

17. The Compton tomography system of claim 1, further comprising a second x-ray optical element comprising a second aperture disposed to receive x-rays from Compton scattering of at least the portion of the planar x-ray beam from the object, the second aperture having a second predetermined depth profile providing a second predetermined angle of view; and
a second x-ray camera disposed to image x-ray photons transmitted by the second x-ray optical element.

18. A Compton tomography method for three-dimensional characterization of an object, comprising:
emitting an x-ray beam;
shaping the x-ray beam into a sheet-like x-ray beam;
directing the x-ray beam towards the object to irradiate a predetermined two-dimensional subset of the object;
imaging Compton-scattered x-rays scattered by the two-dimensional subset of the object by passing the Compton-scattered x-rays through an optical element having an aperture having a first surface and a second surface, the aperture having a depth-dependent profile wherein an outer diameter of the aperture at the first surface and the second surface is larger than an inner diameter at a center of the aperture;
acquiring Compton-scattered images corresponding to a plurality of two-dimensional subsets of the object; and
combining the acquired Compton-scattered images to reconstruct the three-dimensional representation of the object, using a predetermined numerical algorithm.

19. The method of claim 18, wherein the step of shaping the x-ray beam comprises passing the x-ray beam through a ring collimator to shape the x-ray beam into a ring-shaped x-ray beam.

20. The method of claim 18, wherein the step of shaping the x-ray beam comprises passing the x-ray beam through a slit collimator to shape the x-ray beam into a planar x-ray beam.

21. The method of claim 20, wherein the x-ray optical element comprises an array of apertures.

22. The method of claim 21, further comprising recording a separate image from each aperture of the array of apertures.

23. The method of claim 21, further comprising recording a plurality of images using the array of apertures.

24. The method of claim 23, wherein the array of apertures is arranged into a plurality of coded aperture arrays, and wherein each separate image is formed using a corresponding coded aperture array of the plurality of coded aperture arrays.

25. The method of claim 21, wherein the in-plane resolution of the plurality of images is higher than the width of the planar x-ray beam.

26. The method of claim 25, wherein the array of apertures is spaced from the object such that the viewing angle of the apertures of the array is at least 50°.

27. The method of claim 26, wherein the step of imaging the Compton-scattered x-rays comprises measuring an optical density at a plurality of angles to the optical axis of the planar x-ray beams.

28. The method of claim 27, wherein the step of imaging the Compton-scattered x-rays comprises using the measurements of the optical densities to perform a laminographic axial reconstruction of the object.

29. The method of claim 22, wherein an x-ray camera performs the step of recording the separate images using a plurality of detectors, with each detector of the plurality of disposed to capture an image from a corresponding aperture of the array of apertures.

30. The method of claim 22, wherein an x-ray camera performs the step of recording the separate images using a single detector.

31. The method of claim 22, further comprising:
obtaining the separate images; and
combining the separate images into a composite image.

32. The method of claim 21, wherein the aperture array is a coded aperture array.

33. The method of claim 32, wherein the coded aperture array is a uniform redundant array or a modified uniform redundant array.

34. The method of claim 20, wherein the normal vector of the collimator is perpendicular to the normal vector of the aperture.

35. The method of claim 20, further comprising translating the object with respect to the sheet-like x-ray beam and aperture to produce Compton-scattered x-rays from a plurality of slices of the object.

36. The method of claim 20, further comprising translating the sheet-like x-ray beam and the aperture to produce Compton-scattered x-rays from a plurality of slices of the object.

* * * * *